(12) United States Patent
Todo

(10) Patent No.: US 7,098,237 B1
(45) Date of Patent: Aug. 29, 2006

(54) REMEDIES FOR ISCHEMIA REPERFUSION INJURY

(75) Inventor: Satoru Todo, Sapporo (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/807,603

(22) PCT Filed: Oct. 7, 1999

(86) PCT No.: PCT/JP99/05528

§ 371 (c)(1),
(2), (4) Date: Apr. 16, 2001

(87) PCT Pub. No.: WO00/21563

PCT Pub. Date: Apr. 20, 2000

(30) Foreign Application Priority Data

Oct. 14, 1998 (JP) .................................. 10/292423

(51) Int. Cl.
*A61K 31/405* (2006.01)
(52) U.S. Cl. ........................................ 514/419; 514/415
(58) Field of Classification Search ................ 514/419, 514/415, 45
See application file for complete search history.

(56) References Cited

U.S. PATENT DOCUMENTS

| | | | | |
|---|---|---|---|---|
| 5,648,331 A | * | 7/1997 | Koudsi et al. | 514/12 |
| 5,654,326 A | * | 8/1997 | Bach et al. | 514/419 |
| 5,733,916 A | * | 3/1998 | Neely | 514/263.3 |
| 5,986,106 A | * | 11/1999 | Khau et al. | 514/493 |
| 6,214,855 B1 | * | 4/2001 | Gemba et al. | 514/413 |

FOREIGN PATENT DOCUMENTS

| | | |
|---|---|---|
| EP | 0 620 214 A1 | 10/1994 |
| EP | 0 620 215 A1 | 10/1994 |
| EP | 0 672 415 A1 | 2/1995 |
| EP | 0 675 110 A1 | 4/1995 |
| EP | 1 085 021 A1 | 3/2001 |
| WO | WO 96/03120 | 2/1996 |
| WO | WO 96/03376 | 2/1996 |
| WO | WO 96/03383 | 2/1996 |
| WO | WO 97/21664 | 6/1997 |
| WO | WO 97/21716 | 6/1997 |
| WO | WO 98/18464 | 5/1998 |
| WO | WO 98/24437 | 6/1998 |
| WO | WO 98/24756 | 6/1998 |
| WO | WO 98/24794 | 6/1998 |
| WO | WO 98/25609 | 6/1998 |
| WO | WO 99/51605 | 10/1999 |
| WO | WO 99/59999 | 11/1999 |

OTHER PUBLICATIONS

"Preconditioning Protects Against Ischemia-Reperfusion Injury of The Liver", Nilsson, abstract, Digestive Disease Week, 1998.*
Jennifer Daley et al, "Validating Risk-Adjusted Surgical Outcomes: Site Visit Assessment of Process and Structure", J. Am. Coll. Sugr., 185(4):353-364 (1997), Elsevier Science, Inc.
Satoru Todo et al., "Attenuation of Ischemic Liver Injury by Augmentation of Endogenous Adenosine", Transplantation, 63(2):217-223 (1997), Williams & Wilkins.
Naoki Ishizaki et al. "Comparison of Various Lazaroid Compounds for Protection Against Ischemic Liver Injury", Transplantation, 63(2):202-208 (1997), Williams & Wilkins.
Kaoru Koike et al, "Intestinal Ischemia and Type II Phospholipase $A_2$: Preliminary Report", Department of Emergency and Critical Care Medicine , Japan , p. 823(1995).
Kaoru Koike et al., "Intestinal Ischemia and Tyoe II Phospholipase $A_2$ : Preliminary Report", Japan, p. 823 (1995).
Roberta E. Sonnino et al, "Phospholipase $A_2$ Secretion During Intestinal Graft Ischemia", Digestive Diseases and Sciences, 42(5):972-981 (1997) Plenum Publishing Corporation.
Leon J. De Windt et al., "Phospholipase $A_2$-mediated Hydrolysis of Cardiac Phospholipids: The use of Molecular and Transgenic Techniques", Molecular and Cellular Biochemistry 180:65-73 (1998) Kluwer Academic Publishers, printed in the Netherlands.
Jun Takasaki et al., "Antibodies Against Type II Phospholipase $A_2$ Prevent Renal Injury Due to Ischemia and Reperfusion in Rats", FEBS Letters, 440:377-381 (1998) Federation of European Biochemical Societies.
Carol A. Sargent et al., "Effect of the Phospholilphase $A_2$ Inhibitors Quinacrine and 7,7- Dimethyleicosadienoic Acid in Isolated Globaly Ischemic Rat Hearts", The Journal of Pharmacology and Experimental Therapeutics, 262(3):1161-1167 (1992), The American Society for Pharmacology and Experimental Therapeutics.
Yoshiro Shimizu, "Nafamostat Mesilate Rinse Solution—A New Strategy To Prevent Warm Ischemia- Reperfusion Injury In Canine Pancreas Autotransplantation", J. Kyoto Pref. Univ. Med. 107(4), pp. 483-497 (1998).

* cited by examiner

Primary Examiner—Brian-Yong S. Kwon
(74) Attorney, Agent, or Firm—Foley & Lardner LLP

(57) ABSTRACT

A composition for treating or preventing ischemia reperfusion injury which contains an $sPLA_2$ inhibitor as an active ingredient.

1 Claim, 8 Drawing Sheets

REMEDIES FOR ISCHEMIA REPERFUSION INJURY

This Application is a 371 of PCT/JP99/05528 Oct. 07, 1999.

TECHNICAL FIELD

The present invention relates to a composition for treating or preventing ischemia reperfusion injury which contains an sPLA$_2$ inhibitor (a secretion type PLA$_2$ inhibitor), particularly type-II PLA$_2$ inhibitor as an active ingredient.

BACKGROUND ART

In a major operation (surgery), organs are temporarily put into an ischemic condition by ligating the blood vessel directly connected to organs and other method in order to control bleeding. The organs of such artificial ischemia suffer various injuries. Various injuries occur by a variety of causes after reperfusion of the blood in such organs.

Similar problems are encountered in organ transplantation. Extorpation of organs from an individual with cardiac standstill and application of the organs for transplantation (Non-heart Beating Donor Program: NHBD) have been noticed in recent years as a solution of lack of organs for transplantation. However, in the case of hepatic transplantation, for example, 30 minutes of warm ischemia and 12 hours of cold ischemia of the liver are the limit of NHBD for successful hepatic transplantation surgery even by using the latest surgical technology and preservation technology. The proportion of survival of the grafts one year after transplantation is less than 50%. Therefore, it is essential for realization of NHBD to alleviate warm ischemia injury occurred during the period from cardiac standstill to perfusion of the organ with a cold preservation solution, cold ischemia injury occurred thereafter in a cold preservation solution, and tissue injuries related to reperfusion of the blood after transplantation. Drugs having such actions known in the art include endotherin antagonist (J. Am. Coll. Surg., October 1997, Volume 185, 358–364), adenosine antagonist (Transplantation, Vol. 63, 217–223 No. 2, 1997), iron dependent lipid peroxidation inhibitor (Transplantation, Vol. 63, No. 2, p202–208, 1997) and the like.

While the compounds described in EP-620214 (Japanese Patent Laid-open No. 7-010838, U.S. Pat. No. 5,578,634), EP-620215 (Japanese Patent Laid-open No. 7-025850, U.S. Pat. No. 5,684,034), EP-675110 (Japanese Patent Laid-open No. 7-285933, U.S. Pat. No. 5,654,326), WO96/03120 (Japanese Patent Laid-open No. 10-505336), WO96/03376 (Japanese Patent Laid-open No. 10-503208, U.S. Pat. No. 5,641,800), WO96/03383 (Japanese Patent Laid-open No. 10-505584), WO97/21664 (EP-779271), WO97/21716 (EP-779273), WO98/18464 (EP-839806), WO98/24437 (EP-846687), WO98/24756, WO98/24794, WO98/25609, etc., parabromophenacyl bromide, mepaklin, manoaride, cherosin A$_1$, etc. are known as sPLA$_2$ inhibitors, these inhibitors have not been reported to have therapeutic or preventive actions for the ischemia reperfusion injury.

It is known that small intestine PLA$_2$ activity increases by ischemia of the small intestines, and occurrence of lung injury accompanied by reperfusion of the small intestine can be prevented by administration of quinacrine, a PLA$_2$ inhibitor (Am. J. Physiol., 268: G397, 1995). It is also reported that PLA$_2$ which is increased by ischemia of the small intestine is mostly type-II (Journal of Japanese Surgery Association, Vol. 96, No. 12, p823, Dec. 1, 1995). However, these reports only describe prevention of injuries (indirect effects) of other organs such as lung caused by ischemia and reperfusion of local organs (the small intestines), and no descriptions are found about preventive effects (direct effects) of injuries at the local organs such as the small intestines suffering from ischemia. In other words, it is neither known that compounds having an sPLA$_2$ inhibitory action, in particular compounds having type-II PLA$_2$ inhibitory action, are useful as therapeutic or preventive drug for injuries caused in the organs suffering from ischemia, nor is suggested that such compounds are useful for the organs which are transplanted in the transplantation surgery or which may suffer from ischemia during the surgery.

DISCLOSURE OF INVENTION

The present invention provides a composition having a therapeutic or preventive action against ischemia reperfusion injuries.

The present invention relates to I) a composition for treating or preventing ischemia reperfusion injury which contains an sPLA$_2$ inhibitor as an active ingredient.

In more detail, the present invention relates to the following II) to LVI).

II) A composition for treating or preventing ischemia reperfusion injury of I) wherein the sPLA$_2$ inhibitor is a type-II PLA$_2$ inhibitor.

III) A composition for treating or preventing ischemia reperfusion injury of I) which contains a compound as an active ingredient, which is represented by the formula (I):

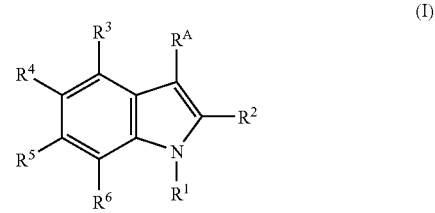

(I)

wherein R$^1$ is a group selected from (a) C7 to C20 alkyl, C7 to C20 alkenyl, C7 to C20 alkynyl, carbocyclic groups, and heterocyclic groups, (b) the groups represented by (a) each substituted independently with at least one group selected from non-interfering substituents, and (c)-(L$^1$)-R$^7$ wherein L$^1$ is a divalent linking group of 1 to 18 atom(s) selected from hydrogen atom(s), nitrogen atom(s), carbon atom(s), oxygen atom(s), and sulfur atom(s), wherein the combination atoms in L$^1$ are selected from the group consisting of i) carbon and hydrogen only, ii) sulfur only, iii) oxygen only, iv) nitrogen and hydrogen only, v) carbon, hydrogen, and sulfur only, and vi) carbon, hydrogen, and oxygen only and R$^7$ is a group selected from the groups (a) and (b);

R$^2$ is hydrogen atom, halogen, C1 to C3 alkyl, C3 to C4 cycloalkyl, C3 to C4 cycloalkenyl, C1 to C3 alkyloxy, or C1 to C3 alkylthio;

R$^3$ and R$^4$ are each independently hydrogen atom, non-interfering substituents, or -(L$^2$)-(acidic group) wherein L$^2$ is an acid linker having an acid linker length of 1 to 5, provided that one of R$^3$ and R$^4$ is -(L$^2$)-(acidic group);

R$^5$ and R$^6$ are each independently hydrogen atom, non-interfering substituents, carbocyclic groups, carbocyclic groups substituted with a non-interfering substituent(s), heterocyclic groups, or heterocyclic groups substituted with a non-interfering substituent(s); and $R^A$ is a group represented by the formula:

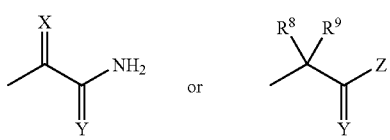

wherein $R^1$ and $R^9$ are each independently hydrogen atom, C1 to C3 alkyl or halogen; X and Y are each independently oxygen atom or sulfur atom; and Z is —$NH_2$ or —$NHNH_2$; the prodrugs thereof; their pharmaceutically acceptable salts; or their hydrates.

IV) A composition for treating or preventing ischemia reperfusion injury of I) which contains a compound as an active ingredient, which is represented by the formula (II):

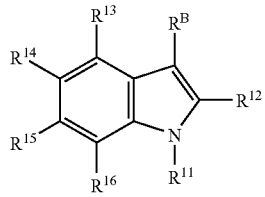

(II)

wherein $R^{11}$ is —$(CH_2)_a$—$R^{10}$ wherein a is an integer from 1 to 6 and $R^{10}$ is a group represented by the formula:

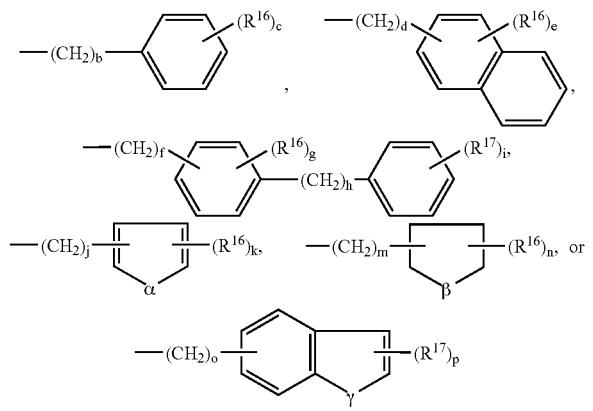

wherein b, d, f, h, j, m, and o are each independently an integer from 0 to 2, $R^{16}$ and $R^{17}$ are each independently halogen, C1 to C10 alkyl, C1 to C10 alkyloxy, C1 to C10 alkylthio, phenyl, or C1 to C10 haloalkyl, α is oxygen atom or sulfur atom, β is —$CH_2$— or —$(CH_2)_2$—, γ is oxygen atom or sulfur atom, c, i, and p are each independently an integer from 0 to 5, e is an integer from 0 to 7, g is an integer from 0 to 4, k and n are each independently an integer from 0 to 3;

$R^{12}$ is halogen, C1 to C3 alkyl, or C3 to C4 cycloalkyl;
$R^{13}$ is hydrogen atom or -($L^3$)-$R^{18}$ wherein $L^3$ is —$OCH_2$—, —$SCH_2$—, —$NHCH_2$—, —$CH_2$—$CH_2$—, —O—$CH(CH_3)$— or —O—$CH(CH_2CH_2Ph)$—, $R^{18}$ is —COOH, —$SO_3H$, or —$P(O)(OH)_2$, and Ph is phenyl;
$R^{14}$ is hydrogen atom or -($L^4$)—$R^{19}$ wherein $L^4$ is a group represented by the formula:

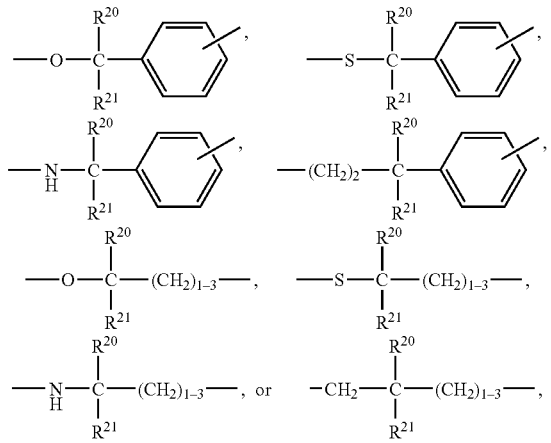

wherein $R^{20}$ and $R^{21}$ are each independently hydrogen atom, C1 to C10 alkyl, C1 to C10 aralkyl, carboxy, alkyloxycarbonyl, or halogen, $R^{19}$ is —COOH, —$SO_3H$, or —$P(O)(OH)_2$, provided that $R^{13}$ and $R^{14}$ are not hydrogen atom at the same time;

$R^{15}$ and $R^{16}$ are each independently hydrogen atom, C1 to C6 alkyl, aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, arylthio, carbocyclic groups, or heterocyclic groups; and $R^B$ is a group represented by the formula:

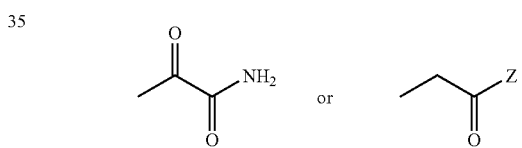

wherein Z is as defined above;

the prodrugs thereof; their pharmaceutically acceptable salts; or their hydrates.

V) A composition for treating or preventing ischemia reperfusion injury of I) which contains a compound as an active ingredient, which is represented by the formula (III):

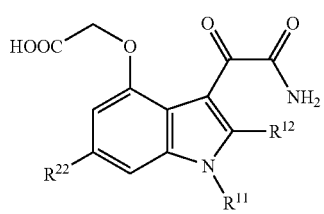

(III)

wherein $R^{11}$ and $R^{12}$ are as defined above;

$R^{22}$ is hydrogen atom, C1 to C6 alkyl, carboxy, carbocyclic groups, or heterocyclic groups;

the prodrugs thereof; their pharmaceutically acceptable salts; or their hydrates.

VI) A composition for treating or preventing ischemia reperfusion injury of I) which contains a compound as an active ingredient, which is represented by the formula (IV):

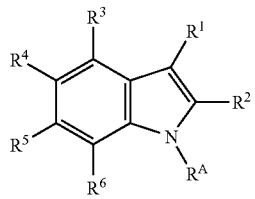

(IV)

wherein $R^1$, $R^2$, $R^3$, $R^4$, $R^5$, $R^6$, and $R^A$ are as defined above, provided that one of $R^3$ and $R^4$ is -($L^2$)-(acidic group);

the prodrugs thereof; their pharmaceutically acceptable salts; or their hydrates.

VII) A composition for treating or preventing ischemia reperfusion injury of I) which contains a compound as an active ingredient, which is represented by the formula (V):

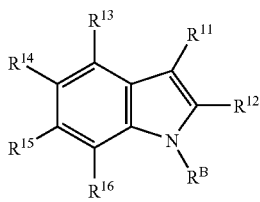

(V)

wherein $R^{11}$, $R^{12}$, $R^{13}$, $R^{14}$, $R^{15}$, $R^{16}$, and $R^B$ are as defined above, provided that $R^{13}$ and $R^{14}$ are not hydrogen atom at the same time;

the prodrugs thereof; their pharmaceutically acceptable salts; or their hydrates.

VIII) A composition for treating or preventing ischemia reperfusion injury of I) which contains a compound as an active ingredient, which is represented by the formula (VI):

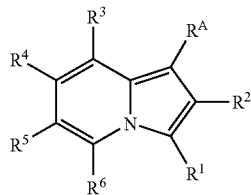

(VI)

wherein $R^1$, $R^2$, $R^3$, $R^4$, $R^5$, $R^6$, and $R^A$ are as defined above, provided that one of $R^3$ and $R^4$ is -($L^2$)-(acidic group);

the prodrugs thereof; their pharmaceutically acceptable salts; or their hydrates.

IX) A composition for treating or preventing ischemia reperfusion injury of I) which contains a compound as an active ingredient, which is represented by the formula (VII):

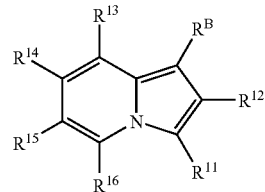

(VII)

wherein $R^{11}$, $R^{12}$, $R^{13}$, $R^{14}$, $R^{15}$, $R^{16}$, and $R^B$ are as defined above, provided that $R^{13}$ and $R^{14}$ are not hydrogen atom at the same time;

the prodrugs thereof; their pharmaceutically acceptable salts; or their hydrates.

X) A composition for treating or preventing ischemia reperfusion injury of I) which contains a compound as an active ingredient, which is represented by the formula (VIII):

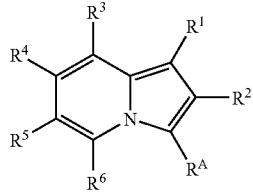

(VIII)

wherein $R^1$, $R^2$, $R^3$, $R^4$, $R^5$, $R^6$, and $R^A$ are as defined above, provided that one of $R^1$ and $R^4$ is -($L^2$)-(acidic group);

the prodrugs thereof; their pharmaceutically acceptable salts; or their hydrates.

XI) A composition for treating or preventing ischemia reperfusion injury of I) which contains a compound as an active ingredient, which is represented by the formula (IX):

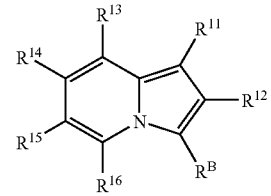

(IX)

wherein $R^{11}$, $R^{12}$, $R^{13}$, $R^{14}$, $R^{15}$, $R^{16}$, and $R^B$ are as defined above, provided that $R^{13}$ and $R^{14}$ are not hydrogen atom at the same time;

the prodrugs thereof; their pharmaceutically acceptable salts; or their hydrates.

XII) A composition for treating or preventing ischemia reperfusion injury of I) which contains a compound as an active ingredient, which is represented by the formula (X):

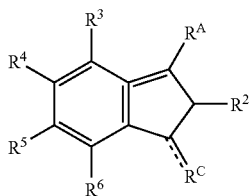

(X)

wherein $R^2$, $R^3$, $R^4$, $R^5$, $R^6$, and $R^A$ are as defined above, a broken line represents the presence or absence of a bond, provided that $R^C$ is the same as defined $R^1$ when a broken line is absence of a bond, $R^C$ is =CH—$R^1$ when a broken line is presence of a bond wherein $R^1$ is as defined above, and one of $R^3$ and $R^4$ is -($L^2$)-(acidic group);

the prodrugs thereof; their pharmaceutically acceptable salts; or their hydrates.

XIII) A composition for treating or preventing ischemia reperfusion injury of I) which contains a compound as an active ingredient, which is represented by the formula (XI):

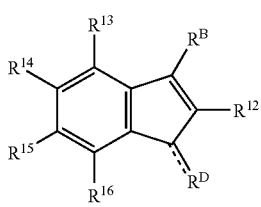

(XI)

wherein $R^{12}$, $R^{13}$, $R^{14}$, $R^{15}$, $R^{16}$, $R^B$, and a broken line are as defined above, provided $R^D$ is the same as defined $R^1$ when a broken line is absence of a bond, $R^D$ is =CH—$(CH^2)_{a-1}$—$R^{10}$ when a broken line is presence of a bond wherein $R^{10}$, $R^{11}$, and a are as defined above, and $R^{13}$ and $R^{14}$ are not hydrogen atom at the same time;

the prodrugs thereof; their pharmaceutically acceptable salts; or their hydrates.

XIV) A composition for treating or preventing ischemia reperfusion injury of I) which contains a compound as an active ingredient, which is represented by the formula (XII):

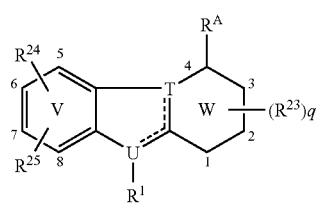

(XII)

wherein $R^1$, $R^A$, and a broken line are as defined above;

$R^{23}$ is non-interfering substituents;

$R^{24}$ is hydroxy or —O—$(CH_2)_r$—$R^E$ wherein $R^E$ is hydrogen atom, cyano, amino, carbamoyl, —$CONR^{26}R^{27}$, —$NHSO_2R^{28}$, or —$CONHSO_2R^{28}$ wherein $R^{26}$ and $R^{27}$ are each independently C1 to C4 alkyl or phenyl(C1 to C4 alkyl), $R^{28}$ is phenyl substituted with carboxy or —COO(C1 to C4 alkyl), phenyl, C1 to C6 alkyl, trifluoromethyl, or -($L^2$)-(acidic group) wherein $L^2$ is as defined above, and r is an integer from 1 to 5;

$R^{25}$ is non-interfering substituents, carbocyclic groups, carbocyclic groups substituted with a non-interfering substituent(s), heterocyclic groups, and heterocyclic groups substituted by a non-interfering substituent(s);

one of T and U is nitrogen atom and the other is carbon atom;

V is benzene ring or pyridine ring wherein the nitrogen atom is at the 5-, 6-, 7-, or 8-position;

W is cyclohexene ring, benzene ring, pyridine ring wherein the nitrogen atom is at the 1-, 2-, or 3-position, or a 6-membered heterocyclic group having one heteroatom selected from the group consisting of sulfur or oxygen at the 1-, 2-, or 3-position, and nitrogen atom at the 1-, 2-, 3-, or 4-position;

q is an integer from 1 to 3;

provided that $R^{24}$ is not —O—$(CH_2)_t$H wherein t is 1 or 2 when $R^{25}$ is hydrogen atom and $R^1$ is benzyl; and W is a 6-membered heterocyclic group having one heteroatom selected from the group consisting of sulfur or oxygen at the 1-, 2-, or 3-position, and nitrogen atom at the 1-, 2-, 3-, or 4-position when T is nitrogen atom;

the prodrugs thereof; their pharmaceutically acceptable salts; or their hydrates.

XV) A composition for treating or preventing ischemia reperfusion injury of I) which contains a compound as an active ingredient, which is represented by the formula (XII):

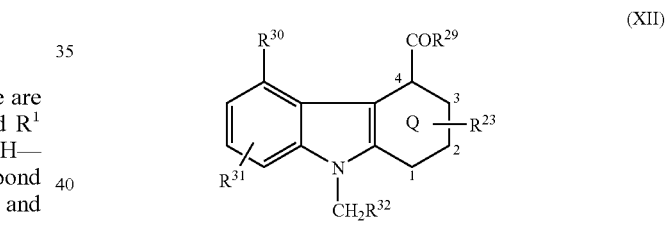

(XII)

wherein $R^{23}$ is as defined above;

$R^{29}$ is —$NHNH_2$ or —$NH_2$;

$R^{30}$ is hydroxy or —O—$(CH_2)_r$—$R^F$ wherein $R^F$ is hydrogen atom, carboxy, carbamoyl, —COO(C1 to C4 alkyl), —P(=O)($R^{33}R^{34}$) wherein $R^{33}$ and $R^{34}$ are each independently hydroxy or —O—(C1 to C4 alkyl), —$SO_3H$, —$SO_3$(C1 to C4 alkyl), tetrazolyl, cyano, amino, —$NHSO_2R^{35}$, or —$CONHSO_2R^{35}$ wherein $R^{35}$ is C1 to C6 alkyl or trifluoromethyl, phenyl, or phenyl substituted with carboxy or —COO(C1 to C4 alkyl), and r is as defined above;

$R^{31}$ is hydrogen atom, —O—(C1 to C4 alkyl), halogen, C1 to C6 alkyl, phenyl, (C1 to C4 alkyl)phenyl, —$CH_2OSi$(C1 to C6 alkyl), furyl, thienyl, C1 to C6 hydroxyalkyl, —$(CH_2)_sR^{36}$ wherein $R^{36}$ is hydrogen atom, carbamoyl, —$NR^{26}NR^{27}$ wherein $R^{26}$ and $R^{27}$ are as defined above, cyano, or phenyl and s is an integer from 1 to 8, or phenyl substituted with C1 to C6 alkyl, halogen, or trifluoromethyl;

$R^{32}$ is hydrogen atom, C5 to C14 alkyl, C3 to C14 cycloalkyl, pyridyl, phenyl, or phenyl substituted with C1 to C6 alkyl, halogen, trifluoromethyl, trifluoromethyloxy, C1 to C4 alkyloxy, cyano, C1 to C4 alkylthio, phenyl(C1 to C4 alkyl), (C1 to C4 alkyl) phenyl, phenyl, phenyloxy, or naphthyl; and Q is cyclohexene ring or benzene ring;

the prodrugs thereof; their pharmaceutically acceptable salts; or their hydrates.

XVI) A composition for treating or preventing ischemia reperfusion injury of I) which contains a compound as an active ingredient, which is represented by the formula (XIII):

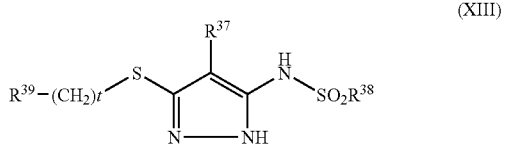

wherein $R^{37}$ is phenyl, isoquinoline-3-yl, pyrazinyl, pyridine-2-yl, or pyridine-2-yl substituted at 4-position with C1 to C4 alkyl, C1 to C4 alkyloxy, cyano, or —(CH2)$_{0-2}$CONH$_2$;

$R^{38}$ is phenyl optionally substituted with 1 to 3 substituents selected from the group consisting of C1 to C4 alkyl, cyano, halogen, nitro, —COO(C1 to C4 alkyl) and trifluoromethyl, naphthyl, or thienyl optionally substituted with 1 to 3 halogen;

$R^{39}$ is halogen, phenyl, phenyl(C2 to C6 alkenyl), pyridyl, naphthyl, quinolyl, (C1 to C4 alkyl)thiazolyl, phenyl substituted with one or two substituents selected from the group consisting of C1 to C4 alkyl, cyano, carbamoyl, nitro, trifluoromethyl, halogen, C1 to C4 alkyloxy, —COO(C1 to C4 alkyl), phenoxy, and —SR$^{40}$ wherein $R^{40}$ is C1 to C4 alkyl or halophenyl, phenyl substituted with one substituent selected from the group consisting of —O—(CH$_2$)$_{1-3}$R$^{41}$ wherein $R^{41}$ is cyano, carboxy, carbamoyl, or tetrazolyl, —OR$^{42}$ wherein $R^{42}$ is cyclopentyl, cyclohexyl, or halogen, and phenyl substituted with C1 to C4 alkoxy or phenyl substituted with methylenedioxy; and t is an integer from 1 to 5;

the prodrugs thereof; their pharmaceutically acceptable salts; or their hydrates.

XVII) A composition for treating or preventing ischemia reperfusion injury of I) which contains a compound as an active ingredient, which is represented by the formula (XIV):

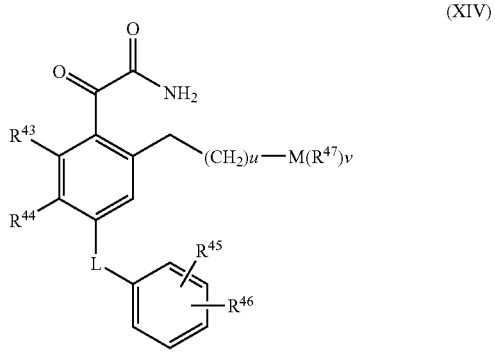

wherein $R^{43}$ and $R^{44}$ are each independently hydrogen atom, halogen, or C1 to C4 alkyl;

$R^{45}$ and $R^{46}$ are each independently hydrogen atom, C1 to C4 alkyl, C1 to C4 alkyloxy, C1 to C4 alkylthio, halogen, phenyl, or phenyl substituted with halogen;

$R^{47}$ is hydrogen atom or C1 to C4 alkyl;

M is —CO$_2$—, —PO$_3$—, or —SO$_3$—;

L is —O— or —(CH$_2$)$_{0-1}$—;

u is an integer from 1 to 8;

provided that v is 1 when M is —CO$_2$— or —PO$_3$—;

v is 1 or 2 when M is —SO$_3$—;

the prodrugs thereof; their pharmaceutically acceptable salts; or their hydrates.

XVIII) A composition for treating or preventing ischemia reperfusion injury of I) which contains a compound as an active ingredient, which is represented by the formula (XV):

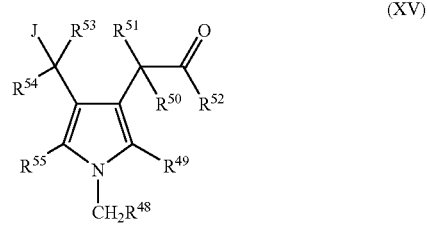

wherein $R^{48}$ is hydrogen atom, C1 to C4 alkyl, phenyl, or phenyl substituted with one or two substituents selected from the group consisting of C1 to C4 alkyl, C1 to C4 alkyloxy, phenyl(C1 to C4 alkyl), C1 to C4 alkylthio, halogen, and phenyl;

$R^{49}$ is hydrogen atom, C1 to C4 alkyl, halogen, C1 to C4 alkyloxy, or C1 to C4 alkylthio;

$R^{50}$ and $R^{51}$ are each independently halogen or $R^{50}$ and $R^{51}$ are taken together to form =O;

$R^{52}$ is —NH$_2$ or —NHNH$_2$;

$R^{53}$ and $R^{54}$ are each hydrogen atom or when one of $R^{53}$ and $R^{54}$ is hydrogen atom, the other is C1 to C4 alkyl or —(CH$^2$)$_{0-4}$—R$^{56}$ wherein $R^{56}$ is —CO$_2$R$^{57}$, —PO$_3$(R$^{57}$)$_2$, —PO$_4$(R57)$_2$, or —SO$_3$R$^{57}$ wherein $R^{57}$ is each independently C1 to C4 alkyl, or $R^{53}$ and $R^{54}$, taken together, are =O or =S;

$R^{55}$ is hydrogen atom, methyl, or ethyl; and

J is $R^{58}$—(C1 to C6 alkyl)-, $R^{58}$—(C2 to C6 alkenyl)-, or phenyl substituted at the ortho position with $R^{58}$ wherein $R^{58}$ is —(CH$_2$)$_{1-4}$R$^{59}$ wherein $R^{59}$ is —CO$_2$R$^{57}$, —PO$_3$(R$^{57}$), —PO$_4$(R$^{57}$)$_2$, or —SO$_3$R$^{57}$ wherein $R^{57}$ is as defined above, and the above phenyl may further be substituted with one or two substituents selected from the group consisting of hydrogen atom, C1 to C4 alkyl, halogen, and C1 to C4 alkyloxy or the above phenyl may be condensed with a phenyl to form a naphthyl group;

the prodrugs thereof; their pharmaceutically acceptable salts; or their hydrates.

XIX) A composition for treating or preventing ischemia reperfusion injury of I) which contains a compound as an active ingredient, which is represented by the formula (XVI):

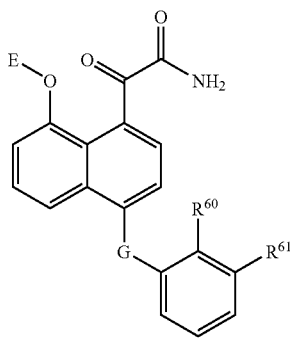

(XVI)

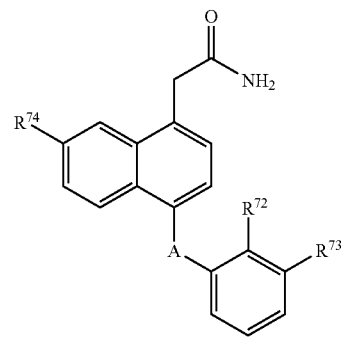

(XVIII)

wherein $R^{60}$ and $R^{61}$ are each independently hydrogen atom or non-interfering substituents, provided that at least one of $R^{60}$ and $R^{61}$ is hydrogen atom;

G is —CH$_2$— or —O—; and

E is —(CH$_2$)$_{1-3}$R$^{62}$ wherein $R^{62}$ is an acidic group selected from —CO$_2$H, —SO$_3$H, and —PO(OH)$_2$;

the prodrugs thereof, their pharmaceutically acceptable salts; or their hydrates.

XX) A composition for treating or preventing ischemia reperfusion injury of I) which contains a compound as an active ingredient, which is represented by the formula (XVII):

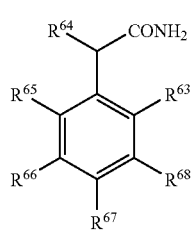

(XVII)

wherein $R^{63}$ is hydrogen atom or —O—(CH$_2$)$_{1-8}$R$^{69}$ wherein $R^{69}$ is —CO$_2$R$^{70}$, —PO$_3$(R$^{70}$)$_2$, or —SO$_3$R$^{70}$ wherein $R^{70}$ is each independently hydrogen atom or C1 to C4 alkyl;

$R^{64}$ is hydrogen atom or hydroxy;

$R^{65}$ and $R^{66}$ are each independently hydrogen atom, halogen, or C1 to C4 alkyl;

one of $R^{67}$ and $R^{68}$ is —B—R$^{71}$ and the other is hydrogen wherein B is —O— or —CH$_2$—, and $R^{71}$ is phenyl or phenyl substituted with one or two substituents selected from the group consisting of halogen, C1 to C4 alkyl, C1 to C4 alkyloxy, phenyl, and phenyl substituted with one or two halogen;

provided $R^{63}$ is hydrogen atom when $R^{68}$ is —B—R$^{71}$;

$R^{71}$ is not phenyl when $R^{63}$, $R^{64}$, $R^{65}$, $R^{66}$, and $R^{68}$ are hydrogen atom and $R^{67}$ is —O—R$^{71}$;

$R^{71}$ is not phenyl substituted with one methoxy group or two chloro groups when $R^{63}$, $R^{64}$, $R^{65}$, $R^{66}$, and $R^{68}$ are hydrogen atom and $R^{67}$ is —CH$_2$—R$^{71}$;

the prodrugs thereof; their pharmaceutically acceptable salts; or their hydrates.

XXI) A composition for treating or preventing ischemia reperfusion injury of I) which contains a compound as an active ingredient, which is represented by the formula (XVIII):

wherein $R^{72}$ and $R^{73}$ are each independently hydrogen atom or non-interfering substituents, provided that at least one of $R^{72}$ and $R^{73}$ is hydrogen atom;

$R^{74}$ is hydrogen atom, —O—(CH)$_{2-4}$—R$^{75}$, —O—[CH(CH$_3$)]$_{2-4}$R$^{75}$, or —O—[CH(CH$_2$CH$_2$C$_6$H$_5$)]$_{2-4}$—R$^{75}$ wherein $R^{75}$ is —CO$_2$H, —PO$_3$H$_2$, or —SO$_3$H$_2$; and A is —O— or —CH$_2$—;

the prodrugs thereof; their pharmaceutically acceptable salts; or their hydrates.

XXII) A composition for treating or preventing ischemia reperfusion injury of I) which contains a compound as an active ingredient, which is represented by the formula (XIX):

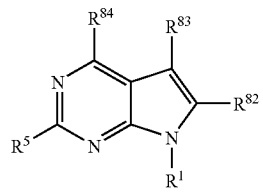

(XIX)

wherein $R^1$ and $R^5$ are as defined above;

$R^{82}$ is hydrogen atom or a group containing 1 to 4 non-hydrogen atoms with necessary hydrogen atom;

$R^{83}$ is -(L$^5$)-R$^A$ wherein L$^5$ is a bond, —CH$_2$—, —O—, —S—, —NH—, or —C(=O) and $R^A$ is as defined above;

$R^{84}$ is -(L$^6$)-(acidic group) wherein L$^6$ is an acid linker;

the prodrugs thereof; their pharmaceutically acceptable salts; or their hydrates.

XXIII) A composition for treating or preventing ischemia reperfusion injury of I) which contains a compound as an active ingredient, which is represented by the formula (XX):

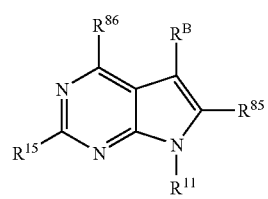

(XX)

wherein $R^{11}$, $R^{15}$, and $R^B$ are as defined above;

$R^{85}$ is hydrogen atom, methyl, ethyl, propyl, isopropyl, cyclopropyl, C1 to C3 alkyloxy, C1 to C3 alkylthio, C1 to C3 haloalkyl, C1 to C3 hydroxyalkyl, or halogen;

$R^{86}$ is -($L^3$)-$R^{18}$ wherein $L^3$ and $R^{18}$ are as defined above;

the prodrugs thereof; their pharmaceutically acceptable salts; or their hydrates.

XXIV) A composition for treating or preventing ischemia reperfusion injury of I) which contains a compound as an active ingredient, which is represented by the formula (XXI):

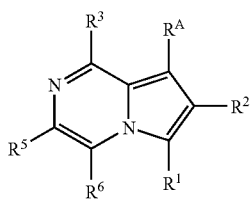

(XXI)

wherein $R^1$, $R^2$, $R^3$, $R^5$, $R^6$, and $R^A$ are as defined above;

the prodrugs thereof; their pharmaceutically acceptable salts; or their hydrates.

XXV) A composition for treating or preventing ischemia reperfusion injury of I) which contains a compound as an active ingredient, which is represented by the formula (XXII):

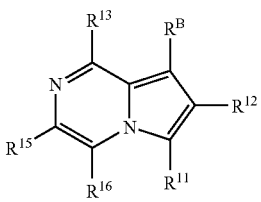

(XXII)

wherein $R^{11}$, $R^{12}$, $R^{13}$, $R^{15}$, $R^{16}$, and $R^B$ are as defined above;

the prodrugs thereof; their pharmaceutically acceptable salts; or their hydrates.

XXVI) A composition for treating or preventing ischemia reperfusion injury of I) which contains a compound as an active ingredient, which is represented by the formula (XXIII):

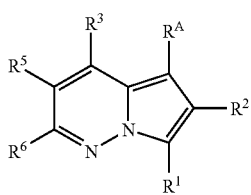

(XXIII)

wherein $R^1$, $R^2$, $R^3$, $R^5$, $R^6$, and $R^A$ are as defined above;

the prodrugs thereof; their pharmaceutically acceptable salts; or their hydrates.

XXVII) A composition for treating or preventing ischemia reperfusion injury of I) which contains a compound as an active ingredient, which is represented by the formula (XXIV):

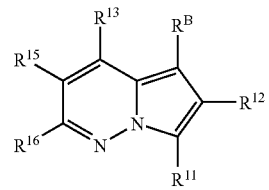

(XXIV)

wherein $R^{11}$, $R^{12}$, $R^{13}$, $R^{15}$, $R^{16}$, and $R^B$ are as defined above;

the prodrugs thereof; their pharmaceutically acceptable salts; or their hydrates.

XXVIII) A composition for treating or preventing ischemia reperfusion injury of I) which contains, as an active ingredient, a compound selected from the group consisting of:

[3-(2-amino-1,2-dioxoethyl)-2-methyl-1-(phenylmethyl)-1H-indole-4-yl]oxy]acetic acid, dl-2-[[3-(2-amino-1,2-dioxoethyl)-2-methyl-1-(phenylmethyl)-1H-indole-4-yl]oxy]propanoic acid,

[[3-(2-amino-1,2-dioxoethyl)-1-([1,1'-biphenyl]-2-yl-methyl)-2-methyl-1H-indole-4-yl]oxy]acetic acid,

[[3-(2-amino-1,2-dioxoethyl)-1-([1,1'-biphenyl]-3-yl-methyl)-2-methyl-1H-indole-4-yl]oxy]acetic acid,

[[3-(2-amino-1,2-dioxoethyl)-1-([1,1'-biphenyl]-4-yl-methyl)-2-methyl-1H-indole-4-yl]oxy]acetic acid,

[[3-(2-amino-1,2-dioxoethyl)-1-[(2,6-dichlorophenyl)methyl]-2-methyl-1H-indole-4-yl]oxy]acetic acid,

[[3-(2-amino-1,2-dioxoethyl)-1-[(4-fluorophenyl)methyl]-2-methyl-1H-indole-4-yl]oxy]acetic acid,

[[3-(2-amino-1,2-dioxoethyl)-2-methyl-1-[(1-naphthyl)methyl]-1H-indole-4-yl]oxy]acetic acid,

[[3-(2-amino-1,2-dioxoethyl)-2-ethyl-1-(phenylmethyl)-1H-indole-4-yl]oxy]acetic acid,

[[3-(2-amino-1,2-dioxoethyl)-2-ethyl-6-methyl-1-(phenylmethyl)-1H-indole-4-yl]oxy]acetic acid,

[[3-(2-amino-1,2-dioxoethyl)-6-carboxy-2-ethyl-1-(phenylmethyl)-1H-indole-4-yl]oxy]acetic acid,

[[3-(2-amino-1,2-dioxoethyl)-1-[(3-chlorophenyl)methyl]-2-ethyl-1H-indole-4-yl]oxy]acetic acid,

[[3-(2-amino-1,2-dioxoethyl)-1-([1,1'-biphenyl]-2-yl-methyl)-2-ethyl-1H-indole-4-yl]oxy]acetic acid,

[[3-(2-amino-1,2-dioxoethyl)-1-([1,1'-biphenyl]-2-yl-methyl)-2-propyl-1H-indole-4-yl]oxy]acetic acid,

[[3-(2-amino-1,2-dioxoethyl)-2-cyclopropyl-1-(phenylmethyl)-1H-indole-4-yl]oxy]acetic acid,

[[3-(2-amino-1,2-dioxoethyl)-1-([1,1'-biphenyl]-2-yl-methyl)-2-cyclopropyl-1H-indole-4-yl]oxy]acetic acid, 4-[[3-(2-amino-1,2-dioxoethyl)-2-ethyl-1-(phenylmethyl)-1H-indole-5-yl]oxy]butanoic acid, 2-[[1-(2-amino-1,2-dioxoethyl)-2-ethyl-3-phenylmethyl-indolizine-8-yl]oxy]acetic acid, 2-[[1-(2-amino-1,2-dioxoethyl)-3-(2-biphenyl)methyl-2-ethylindolizine-8-yl]oxy]acetic acid, 2-[[1-(2-amino-1,2-dioxoethyl)-3-(2-biphenyl)methyl-2-cyclopropylindolizine-8-yl]oxy]acetic acid, 2-[[3-(2-amino-2-oxoethyl)-2-ethyl-1-phenylmethylene-1H-indene-4-yl]oxy]acetic acid, 2-[[3-(2-amino-2-oxoethyl)-2-ethyl-1-(1-naphthyl)methylene-1H-indene-4-yl]oxy]acetic acid, 2-[[8-(2-amino-1,2-dioxoethyl)-7-ethyl-3-methyl-6-phenylmethyl-[1,2-a]pyrazine-1-yl]oxy]acetic acid, 2-[[8-(2-amino-1,2-dioxoethyl)-7-ethyl-3-methyl-6-(2-biphenyl)methyl-[1,2-a]pyrazine-1-yl]oxy]acetic acid, 2-[[8-(2-amino-1,2-dioxoethyl)-6-cyclopropylmethyl-7-ethyl-3-methyl-[1,2-a]pyrazine-1-yl]oxy]acetic acid, 2-[[8-(2-amino-1,2-dioxoethyl)-7-ethyl-3-phenyl-6-phenylmethyl-[1,2-a]pyrazine-1-yl]oxy]acetic acid, 2-[[5-(2-amino-1,2-dioxoethyl)-6-ethyl-7-phenylmethyl-[1,2-b]pyridazine-4-yl]oxy]acetic acid, 2-[[5-(2-amino-1,2-dioxoethyl)-2,6-dimethyl-7-phenylmethyl-[1,2-b]pyridazine-4-yl]oxy]acetic acid, 2-[[5-(2-amino-1,2-dioxoethyl)-6-ethyl-2-phenyl-7-phenylmethyl-[1,2-b]pyridazine-4-yl]oxy]acetic acid, and (5-carbamoyl-9-cyclohexylmethyl-9H-carbazole-4-yl-oxy) acetic acid, and the prodrugs thereof; their pharmaceutically acceptable salts; or their hydrates.

XXIX) A composition for treating or preventing ischemia reperfusion injury of I) which contains a compound as an active ingredient, which is represented by the formula:

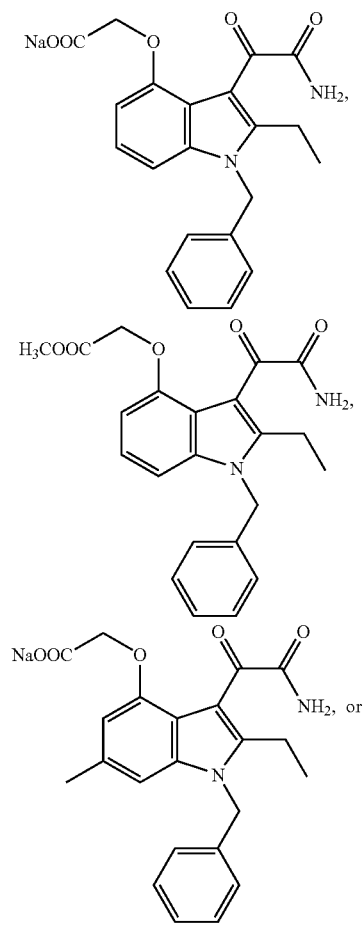

-continued

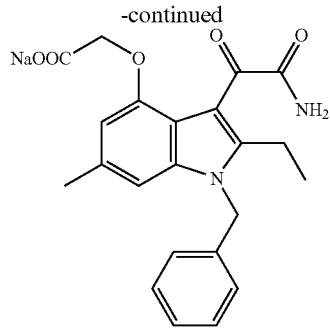

or their hydrates.

XXX) A preservation solution for an organ in an ischemic condition caused by surgery or cardiac standstill, which comprises an sPLA$_2$ inhibitor.

XXXI) A preservation solution for an organ extirpated from a donor for organ transplantation, which comprises an sPLA$_2$ inhibitor.

XXXII) A preservation solution of XXX) or XXXI), wherein the sPLA$_2$ inhibitor is type-II PLA$_2$ inhibitor.

XXXIII) A preservation solution of XXX) or XXXI), wherein the sPLA$_2$ inhibitor is a compound of any one of III) to XXIX).

XXXIV) A preservation solution of any one of XXX) to XXXIII) wherein the organ is heart, liver, pancreas, kidney, or small intestine.

XXXV) A method for preventing ischemia reperfusion injury, which comprises administrating an sPLA$_2$ inhibitor.

XXXVI) A method for preventing ischemia reperfusion injury, which comprises administrating an sPLA$_2$ inhibitor before the occurrence of ischemia caused by surgery or cardiac standstill.

XXXVII) A method for preventing ischemia reperfusion injury for an organ in an ischemic condition caused by surgery or cardiac standstill, which comprises using a solution including an sPLA$_2$ inhibitor as a preservation solution.

XXXVIII) A method for preventing ischemia reperfusion injury, which comprises administration of an sPLA$_2$ inhibitor before reperfusion of blood to an organ which is in an ischemic condition caused by surgery or cardiac standstill.

XXXIX) A method for preventing ischemia reperfusion injury, which comprises administration of an sPLA$_2$ inhibitor after reperfusion of blood to an organ which is in an ischemic condition caused by surgery or cardiac standstill.

XL) A method for preventing ischemia reperfusion injury of any one of XXXV) to XXXIX), wherein the sPLA$_2$ inhibitor is type-II PLA$_2$ inhibitor.

XLI) A method for preventing ischemia reperfusion injury of any one of XXXV) to XXXIX), wherein the sPLA$_2$ inhibitor is a compound of any one of III) to XXIX).

XLII) A method for preventing ischemia reperfusion injury of any one of XXXVII) to XLI) wherein the organ is heart, liver, pancreas, kidney, or small intestine.

XLIII) A method for treating ischemia reperfusion injury, which comprises administrating an sPLA$_2$ inhibitor.

XLIV) A method for treating ischemia reperfusion injury for an organ in an ischemic condition caused by surgery or cardiac standstill, which comprises using a solution including an sPLA$_2$ inhibitor as a preservation solution.

XLV) A method for treating ischemia reperfusion injury, which comprises administrating an sPLA$_2$ inhibitor before the occurrence of ischemia caused by surgery or cardiac standstill.

XLVI) A method for preventing ischemia reperfusion injury, which comprises administrating an sPLA$_2$ inhibitor after reperfusion of blood to an organ which is in an ischemic condition caused by surgery or cardiac standstill.

XLVII) A method for treating ischemia reperfusion injury of any one of XLIII) to XLVI), wherein the sPLA$_2$ inhibitor is type-II PLA$_2$ inhibitor.

XLVIII) A method for treating ischemia reperfusion injury of any one of XLIII) to XLVI), wherein the sPLA$_2$ inhibitor is a compound of any one of III) to XXIX).

IL) A method for treating ischemia reperfusion injury of any one of XLIV) to XLVIII) wherein the organ is heart, liver, pancreas, kidney, or small intestine.

L) A preservation method for an extirpated organ which comprises using a solution including an sPLA$_2$ inhibitor as a preservation solution.

LI) A preservation method of L), wherein the sPLA$_2$ inhibitor is type-II PLA$_2$ inhibitor.

LII) A preservation method of L), wherein the sPLA$_2$ inhibitor is a compound of any one of III) to XXIX).

LIII) A preservation method of L), wherein the organ is heart, liver, pancreas, kidney, or small intestine.

LIV) Use of sPLA$_2$ inhibitor for the preparation of a pharmaceutical composition for treating or preventing ischemia reperfusion injury.

LV) Use of type-II PLA$_2$ inhibitor for the preparation of a pharmaceutical composition for treating or preventing ischemia reperfusion injury.

LVI) Use of a compound of any one of III) to XXIX) for the preparation of a pharmaceutical composition for treating or preventing ischemia reperfusion injury.

The term "ischemia reperfusion injury" as used in the present specification refers to an injury of organs caused by putting the organs into an ischemic condition by surgery or cardiac standstill and/or an jnjury of organ occurred after reperfusion. Preferably, the organ put into the ischemic condition and the injured organ are the same. Such injuries include warm ischemia injury occurred during the period from cardiac standstill to perfusion of the organ with cold preservation solution, cold ischemia injury subsequently occurred in the preservation solution, and injuries of the tissue related to reperfusion of the blood after the transplantation for the organ transplantation.

The term "organs in an ischemic condition by surgery or cardiac standstill" as used in the present specification refers to the organs in the body being in an ischemic condition by surgery or cardiac standstill, or the organs extirpated under ischemic condition caused by surgery or cardiac standstill. The organ which is extirpated from a donor can be referred particularly in the surgery for organ transplantation.

The term "preservation solution" as used in the present specification refers to a solution for preserving organs that may include other pharmaceutically active ingredients (for example a protease inhibitor such as FOY and an immunosuppressive agent) and stabilizers.

The term "organ" as used in the present specification refers to an organ that suffers ischemia during surgery or an organ that can be used for organ transplantation. Such organs include heart, liver, pancreas, kidney, small intestines, etc. The preferable organs are heart, liver, pancreas and kidney, and more preferably the organ is liver.

The term "administration of the sPLA$_2$ inhibitor before occurrence of ischemia caused by surgery or cardiac standstill" as used herein refers to administering the sPLA$_2$ inhibitor before clamping the artery and vein directly connected to the organ in order to prevent a large quantity of bleeding, etc. during operation, or administering the sPLA$_2$ inhibitor before cardiac standstill of the donor during the surgery for organ transplantation. The administration methods include intravenous injection, oral administration, etc.

The term "using the solution containing the sPLA$_2$ inhibitor as a preservation solution" as used in the present specification refers to using a solution containing the sPLA$_2$ inhibitor as a preservation solution of the organs whose directly connected arteries or veins being ligated at an operation, and using a solution containing the sPLA$_2$ inhibitor as a preservation solution of the organ before organ transplantation extirpated from a donor to a recipient at a surgery for organ transplantation. The preservation methods include simply allowing the organ to contact with the preservation solution, perfusion of the preservation solution to the organ, etc.

The term "administering the sPLA$_2$ inhibitor before reperfusion of the blood to an organ in an ischemic condition by surgery or cardiac standstill" as used in the present specification refers, for example, to administering the sPLA$_2$ inhibitor in the body before reperfusion so that the sPLA$_2$ inhibitor can reach the organ in an ischemic condition by surgery immediately after starting reperfusion of the blood to the organ, administering the sPLA$_2$ inhibitor to a recipient in the surgery for organ transplantation and others before transplantation of the organ. The administration methods include intravenous injection, oral administration, etc.

The term "administering the sPLA$_2$ inhibitor to an organ in an ischemic condition by surgery or cardiac standstill after reperfusion of the blood" as used in the present specification refers, for example, to administering the sPLA$_2$ inhibitor to the organ in the ischemic condition by surgery after reperfusion of the blood, administering the sPLA$_2$ inhibitor to the organ after transplantation of the organ to a recipient in the organ transplantation surgery and others. The administration methods include intravenous injection, oral administration, etc.

The term "a method for preservation of an organ characterized in that extirpated organ is preserved by using the preservation solution containing the sPLA$_2$ inhibitor" as used in the present specification refers to a preservation method of the organ by allowing the organ to contact with the preservation solution containing the sPLA$_2$ inhibitor, a perfusion method of the preservation solution containing the sPLA$_2$ inhibitor into the extirpated organ and other method.

When a compound having a therapeutic or preventive effect for ischemia reperfusion injury has acidic or basic functional groups, various physiologically adequate salts of the compound having higher water solubility can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like. In case of forming a hydrate, a questioned compound may be coordinated with a suitable number of water molecules.

In the case where a compound having a therapeutic or preventive action against ischemia reperfusion injuries has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner.

Prodrug is a derivative of the compound having a therapeutic or preventive action against ischemia reperfusion injuries and a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. Particularly preferred prodrugs are C1–C6 alkyl ester of acidic derivatives such as methyl ester and ethyl ester. Double ester such as (acyloxy) alkyl ester or ((alkyloxycarbonyl)oxy)alkyl ester type prodrugs may be optionally manufactured.

The term "sPLA$_2$ inhibitor" as used in the present specification refers to an inhibitor that can prevent or therapeutically significantly reduce decomposition of cell membrane phospholipids initiated by sPLA$_2$. Specific examples of the inhibitor include the compounds represented by the foregoing general formula (I) to (XXIV), the compounds exemplified by the foregoing general formula (XXVIII) and (XXIX), and the compounds represented by the following formula:

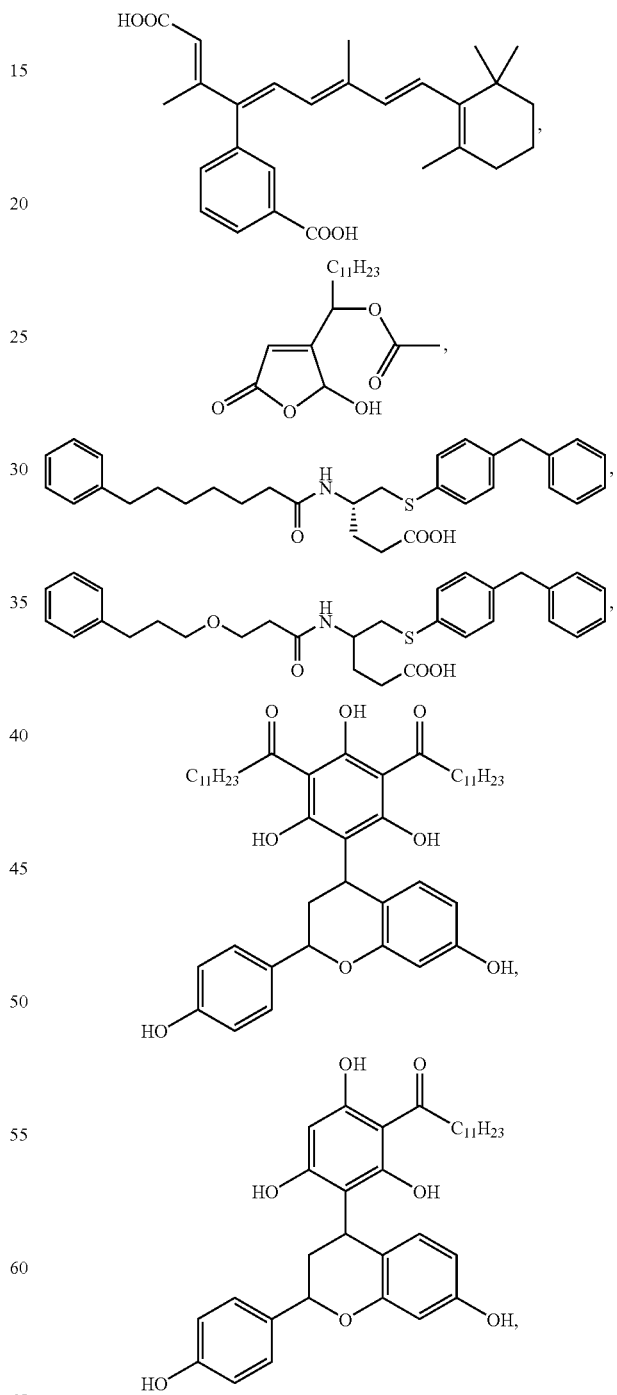

-continued

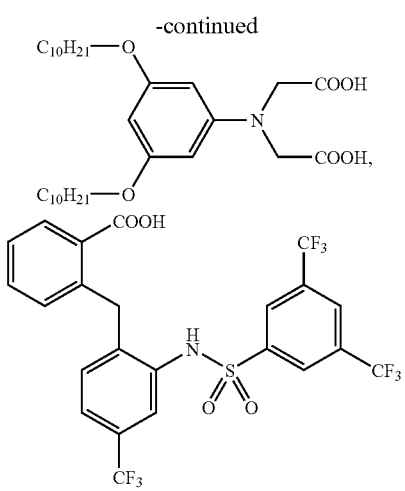

The term "type II PLA$_2$ inhibitor" as used in the present specification refers to an inhibitor that can prevent or therapeutically significantly reduce decomposition of cell membrane phospholipids initiated by type-II PLA$_2$.

The term "pharmaceutically acceptable" as used in the present specification refers to a carrier, diluent or additive that is compatible with other ingredients in the formulation and is not harmful to recipients.

The treating or preventing composition of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound having a therapeutic or preventive action against ischemia reperfusion injuries of this invention prior to administration.

Any suitable carrier which has been well known by those skilled in the art may be used for the formulation. In such formulation, a carrier is in the form of solid, liquid, or a mixture of solid and liquid. For instance, a compound having a therapeutic or preventive action against ischemia reperfusion injuries is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The compound having a therapeutic or preventive action against ischemia reperfusion injury may be dissolved or suspended in a pharmaceutically acceptable carrier such as sterilized water, sterilized organic solvent or a mixture thereof for use as a preservation solution. Other compositions suitable for preservation of organs may be added in the preservation solution. Required concentration of the preservation solution is, for example, 0.01 mol/L to 100 mol/L, preferably 0.1 mol/L to 10 mol/L, which is a concentration showing protective effect on organs.

An appropriate dosage varies with the conditions of the patients, an administration route, their age, and their body weight. In the case of intravenous injection to an adult, the dosage can generally be between 0.01–10 mg/kg/day, preferably 0.1–1 mg/kg/day.

In the present specification, the term "alkyl" employed alone or in combination with other terms means a straight or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes cycloalkyl (such as cyclopropyl, cyclobutyl, cyclopentyl, cyclohexyl, cycloheptyl, and cyclooctyl); cycloalkenyl (such as cyclobutylenyl, cyclopentenyl, cyclohexenyl, cycloheptenyl, and cyclooptenyl); phenyl, naphthyl, norbornyl, bicycloheptadienyl, indenyl, stilbenyl, terphenylyl, phenylcyclohexenyl, acenaphthyl, anthoryl, biphenylyl, bibenzylyl, and a phenylalkylphenyl derivative represented by the formula (XXV):

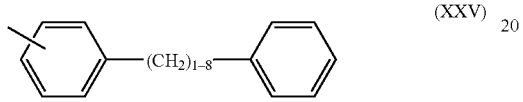

Phenyl, cyclohexyl or the like is preferred as a carbocyclic group in the $R^5$, $R^6$, $R^{15}$, $R^{16}$, $R^{22}$, and $R^{25}$.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, furanyl, benzofuranyl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl and the like.

Pyridyl, thienyl or the like is preferred as a heterocyclic group in the $R^5$, $R^6$, $R^{15}$, $R^{16}$, $R^{22}$, and $R^{25}$.

Preferred carbocyclic and heterocyclic groups in $R^1$ are a group represented by the formula:

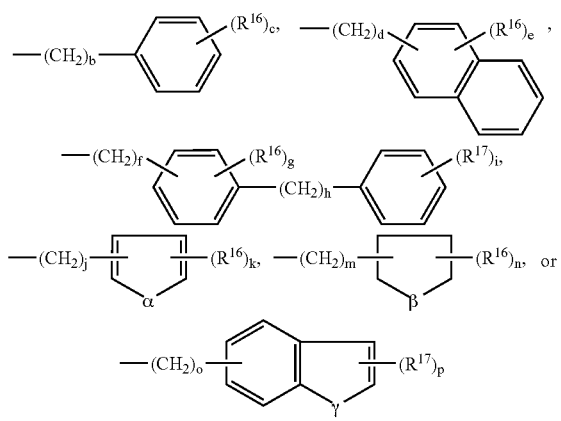

wherein b, d, f, h, j, n, and o are each independently an integer from 0 to 2, $R^{16}$ and $R^{17}$ are each independently halogen, C1 to C10 alkyl, C1 to C10 alkyloxy, C1 to C10 alkylthio, phenyl, or C1 to C10 haloalkyl, α is oxygen atom or sulfur atom, β is —$CH_2$— or —$(CH_2)_2$—, γ is oxygen atom or sulfur atom, c, i, and p are each independently an integer from 0 to 5, e is an integer from 0 to 7, g is an integer from 0 to 4, k and n are each independently an integer from 0 to 3. When the above c, e, f, g, i, k, n, and/or p are 2 or more, a plural number of $R^{16}$ or $R^{17}$ may be different from one another. When $R^{16}$ is a substituent on the naphthyl group, the substituent may be substituted at any arbitrary position on the naphthyl group. A more preferable example includes a group represented by the formula:

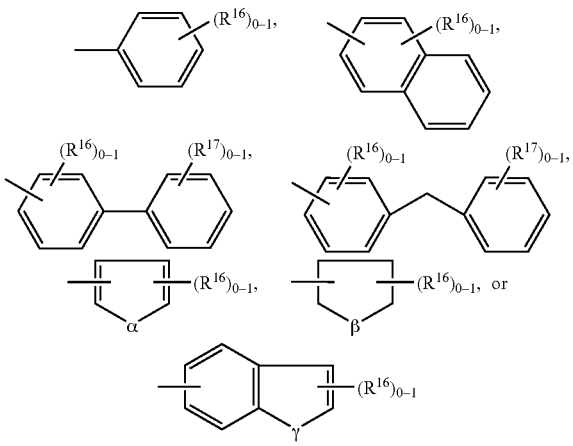

wherein $R^{16}$, $R^{17}$, α, β, and γ are the same as defined above. When $R^{16}$ is a substituent on the naphthyl group, the substituent may be substituted at any arbitrary position on the naphthyl group.

The term "non-interfering substituent" in the present specification means a group suitable for substitution of the above described "carbocyclic group", "heterocyclic group", and a skelton. An example of the non-interfering substituents includes C1 to 10 alkyl, C2 to C6 alkenyl, C2 to C6 alkynyl, C7 to C12 aralkyl (such as benzyl and phenethyl), C7 to C12 alkaryl, C3 to C8 cycloalkyl, C3 to C8 cycloalkenyl, phenyl, tolyl, xylyl, biphenylyl, C1 to C10 alkyloxy, C1 to C6 alkyloxy C1 to C6 alkyl (such as methyloxymethyl, ethyloxymethyl, methyloxyethyl, and ethyloxyethyl), C1 to C6 alkyloxy C1 to C6 alkyloxy (such as methyloxymethyloxy and methyloxyethyloxy), C1 to C6 akyloxycarbonyl (such as methylcarbonyl and ethylcarbonyl), C1 to C6 alkylcarbonylamino (such as methylcarbonylamino and ethylcarbonylamino), C1 to C6 alkyloxyamino (such as methyloxyamino and ethyloxyamino), C1 to C6 alkyloxyaminocarbonyl (such as methyloxyaminocarbonyl and ethyloxyaminocarbonyl), mono or di C1 to C6 alkylamino (such as methylamino, ethylamino, dimethylamino, and ethylmethylamino), C1 to C10 alkylthio, C1 to C6 alkylthiocarbonyl (such as methylthiocarbonyl and ethylthiocarbonyl), C1 to C6 alkylsulfinyl (such as methylsulfinyl and ethylsulfinyl), C1 to C6 alkylsulfonyl (such as methylsulfonyl and ethylsulfonyl), C2 to C6 haloalkyloxy (such as 2-chloroethyloxy and 2-bromoethyloxy), C1 to C6 haloalkylsulfonyl (such as chloromethylsulfonyl and bromomethylsulfonyl), C1 to C10 haloalkyl, C1 to C6 hydroxyalkyl (such as hydroxymethyl and hydroxyethyl), C1 to C6 alkyloxycarbonyl (such as methyloxycarbonyl and ethyloxycarbonyl), —(CH$_2$)$_{1-8}$—O—(C1 to C6 alkyl), benzyloxy, aryloxy (such as phenyloxy), arylthio (such as phenylthio), —(CONHSO$_2$R$^{76}$), —CHO, amino, amidino, halogen, carbamyl, carboxy, carbalkyloxy, —(CH$_2$)$_{1-8}$—COOH (such as carboxymethyl, carboxyethyl, and carboxypropyl), cyano, cyanoguanidino, guanidino, hydrazido, hydrazino, hydroxy, hydroxyamino, nitro, phosphono, —SO$_3$H, thioacetal, thiocarbonyl, C1 to C6 carbonyl, carbocyclic groups, heterocyclic groups and the like wherein R$^{76}$ is C1 to C6 alkyl or aryl. These groups may be substituted with at least one substituent selected from the group consisting of C1 to C6 alkyl, C1 to C6 alkyloxy, C2 to C6 haloalkyloxy, C1 to C6 haloalkyl, and halogen.

Preferable are halogen, C1 to C6 alkyl, C1 to C6 alkyloxy, C1 to C6 alkylthio, and C1 to C6 haloalkyl as the "non-interfering substituent" in "substitued with non-interfering substituent" in the R$^1$, R$^5$, R$^6$, and R$^{25}$. More preferable are halogen, C1 to C3 alkyl, C1 to C3 alkyloxy, C1 to C3 alkylthio, and C1 to C3 haloalkyl.

Preferable are C1 to C6 alkyl, aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, arylthio, carbocyclic groups, and heterocyclic groups as the "non-interfering substituents" in the R$^3$, R$^4$, R$^5$, R$^6$, R$^{23}$, R$^{25}$, R$^{60}$, R$^{61}$, R$^{72}$, and R$^{73}$. More preferable are C1 to C6 alkyl, aralkyl, carboxy, C1 to C6 hydroxyalkyl, phenyl, and C1 to C6 alkyloxycarbonyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a basic structure through a suitable linking atom (hereinafter defined as "acid linker"). An example of the acidic group includes a group represented by the formula:

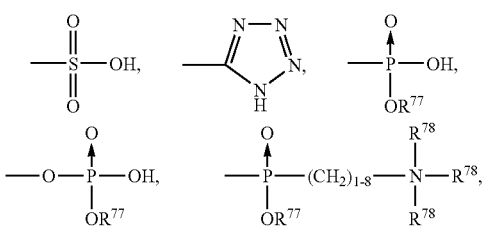

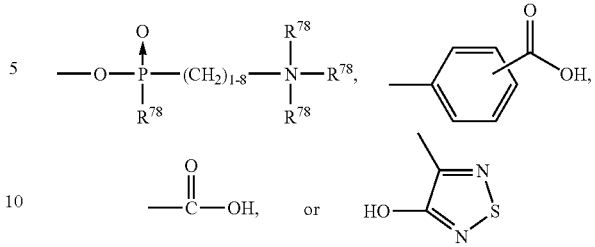

wherein R$^{77}$ is hydrogen atom, a metal, or C1 to C10 alkyl and each R$^{78}$ is independently hydrogen atom or C1 to C10 alkyl. Preferable is —COOH, —SO$_3$H, or P(O)(OH)$_2$. More preferable is —COOH.

The term "acid linker" in the present specification means a divalent linking group represented by a symbol -(L$^2$)-, and it functions to join a basic structure to an "acidic group" in the general relationship. An example of it includes a group represented by the formula:

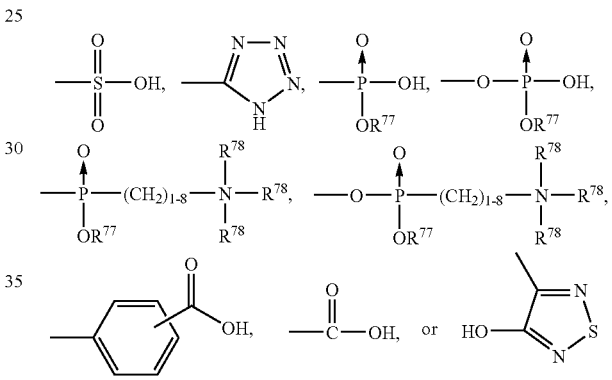

wherein M is —CH$_2$—, —O—, —N(R$^{81}$)—, or —S—, and R$^{79}$ and R$^{80}$ are independently hydrogen atom, C1 to C10 alkyl, aryl, aralkyl, carboxy, or halogen. Preferable are —O—CH$_2$—, —S—CH$_2$—, —N(R$^{81}$)—CH$_2$—, —CH$_2$—CH$_2$—, —O—CH(CH$_3$)—, or —O—CH((CH$_2$)$_2$Ph)— wherein R$^{81}$ is C1 to C6 alkyl and Ph is phenyl. More preferable is —O—CH$_2$— or —S—CH$_2$—.

In the present specification, the term "acid linker length" means the number of atoms (except for hydrogen atoms) in the shortest chain of a linking group -(L$^2$)- which connects a basic structure with the "acidic group". The presence of a carbocyclic ring in -(L$^2$)- counts as the number of atoms approximately equivalent to the calculated diameter of the carbocyclic ring. Thus, a benzene and cyclohexane ring in the acid linker counts as two atoms in culculating the length of -(L$^2$)-. A preferable length is 2 to 3.

The term "haloalkyl" in the present specification means the above described "alkyl" substituted with the above described "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2,2,2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl (such as 3-phenylpropyl), naphthylmethyl (such as 1-naphthylmethyl) and the like.

An example of the "alkyloxycarbonyl" in the present specification includes methyloxycarbonyl, ethyloxycarbonyl, n-propyloxycarbonyl and the like.

An example of the "aryloxy" in the present specification includes phenyloxy and the like.

An example of the "arylthio" in the present specification includes phenylthio and the like.

The term "halophenyl" in the present specification includes a phenyl substituted with one or more above mentioned "halogen". An example of it includes fluorophenyl, chlorophenyl, bromophenyl, iodophenyl, difluorophenyl, dichlorophenyl, dibromophenyl, trifluorophenyl, trichlorophenyl, tribromophenyl, chlorofluorophenyl, bromochlorophenyl, and the like.

BEST MODE FOR CARRYING OUT THE INVENTION

Figure 1:
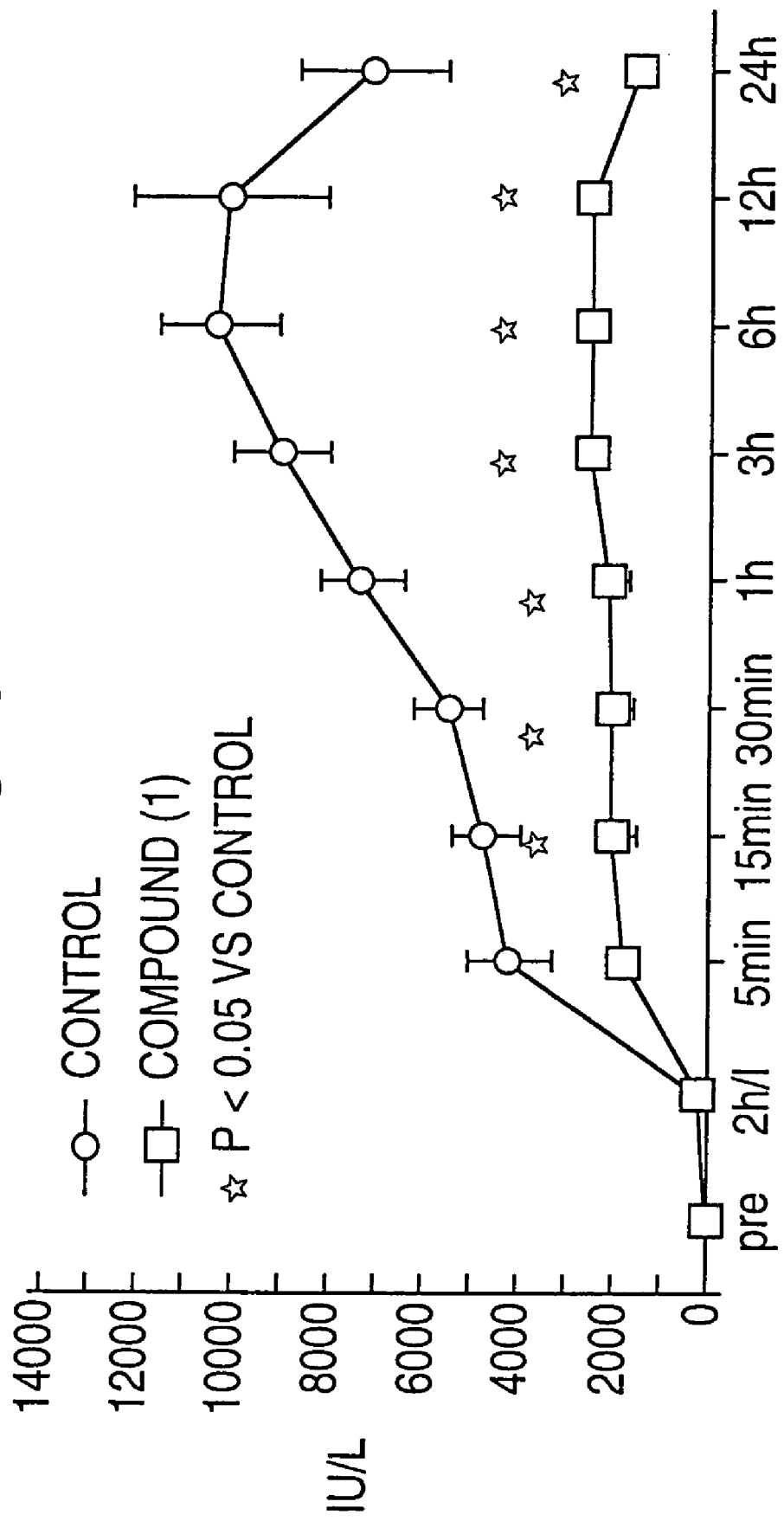
FIG. 1 is a graph showing the change of AST as an index of hepatic functions, wherein the axis of ordinate shows the measured values (in IU/L) and the axis of abscissa shows the time (the time 2 h/I means 2 hours after ischemia and the others represent the time after perfusion).

The action of the composition for treating or preventing ischemia reperfusion injury according to the present invention was investigated as follows.

Beagle dogs (female, 10 to 12 kg) are used for experimental animals. Under the control of general anesthesia by inserting a tube into the trachea, a bypass is formed between the portal vein, femoral vein and external jugular vein. After completely ablating the perihepatic band, the hepatoduodental ligament and inferior vena cava on and under liver are respectively clumped to prepare so called Total Hepatic Vascular Exclusion Model. An auxiliary circulation is applied during this two hour's operation. Ischemia is continued for two hours, and reperfusion of the blood is resumed by releasing the clump. Various physiological changes are confirmed under laparotomy until three hours after reperfusion and thereafter abdomen is sutured (the method for maintaining anesthesia during this period follows the existing protocol, and fluctuation of the blood pressure and the like are not corrected by different anesthetic methods). Survival at two weeks after the surgery is confirmed.

The test compound is administered before and after warm ischemia. The compound is administered by intravenous injection.

Various factors related to the hepatic function and blood flow of hepatic tissues were measured by sampling over time from the peripheral artery and hepatic vein.

Tissue injury caused by 12 hour's cold ischemia has been known to correspond to the injury caused by one hour's warm ischemia. Therefore, the experimental system according to the present invention can assume one hour's warm ischemia in the organ transplantation surgery and 12 hour's cold preservation of the organ.

The compounds represented by the general formula (I) to (XX) can be synthesized by the methods known in the art described in EP-620214 (Japanese Patent Laid-open No. 7-010838, U.S. Pat. No. 5,578,634), EP-620215 (Japanese Patent Laid-open No. 7-025850, U.S. Pat. No. 5,684,034), EP-675110 (Japanese Patent Laid-open No. 7-285933, U.S. Pat. No. 5,654,326), WO96/03120 (Japanese Patent Laid-open No. 10-505336), WO96/03376 (Japanese Patent Laid-open No. 10-503208, U.S. Pat. No. 5,641,800), WO96/03383 (Japanese Patent Laid-open No. 10-505584), WO97/21664 (EP-779271), WO97/21716 (EP-779273), WO98/18464 (EP-839806), WO98/24437 (EP-846687), WO98/24756, WO98/24794, WO98/25609 and the like.

The compounds represented by the general formula (XXI) to (XXII) can be synthesized by the schemes described below.

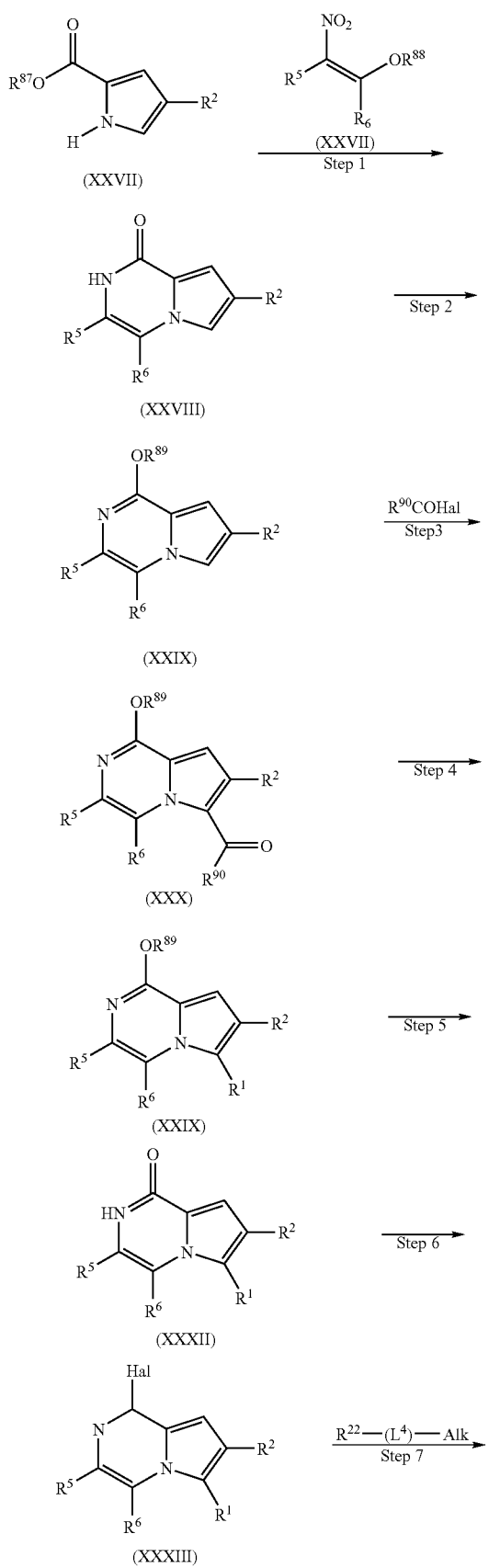

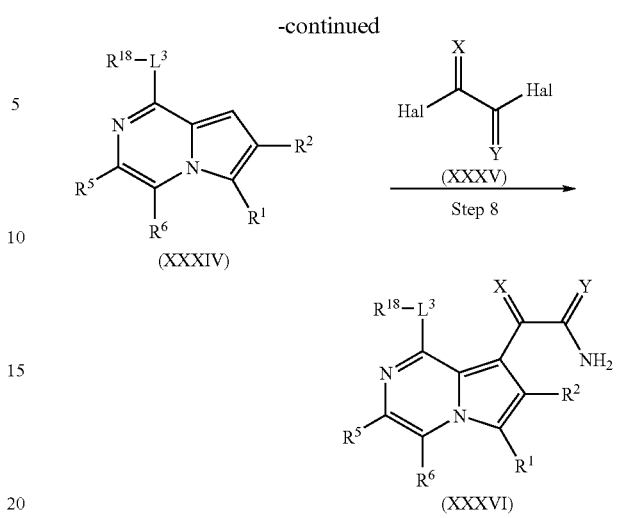

wherein $R^1$, $R^2$, $R^5$, $R^6$, $R^{18}$, X, Y, and $L^3$ are as defined above; $R^{87}$, $R^{88}$ and $R^{89}$ are C1 to C3 alkyl; $R^{90}$ is a residue of $R^1$; Hal is a halogen; and Alk is an alkali metal.

(Step 1)

The present step is the one for constructing pyrrolo[1,2-a]pyrazine ring, and it may be conducted in accordance with a process described in J. Chem. Soc., Perkin Trans. 1, 1990, 311–314.

(Step 2)

The present step is the one for transforming the ketone at 1-position into an alkyloxy group. To the compound (XXVII) is added a halogenating agent such as phosphorus oxychloride, phenylphosphonic dichloride and the like, and the resulting mixture is refluxed for 1 to 8 hours, preferably 3 to 5 hours. The resulting compound is dissolved in an alcohol (for example, methanol, ethanol, and n-propanol), an alkali metal compound of C1 to C3 alcohol (for example, sodium methoxide, and sodium ethoxide), sodium p-toluenesulfinate and the like are added to the solution, and the mixture is stirred at 70° C. to 120° C., preferably 80° C. to 100° C. for 5 to 36 hours, preferably 12 to 24 hours. When the resulting product is subjected to a usual work-up, the compound (XXIX) can be obtained.

(Step 3)

The present step is the one for introducing a substituent to 6-position of pyrrolo[1,2-a]pyrazine, and it may be carried out by Friedel-Crafts reaction. The compound (XXIX) is dissolved in a solvent such as 1,2-dichloroethane, methylene chloride and the like, $R^{90}$COHal and Lewis acid (for example, $AlCl_3$, $SbF_5$, $BF_3$ and the like) are added gradually to the solution at −78° C. to 10° C., preferably −20° C. to ice-cooling, and the resulting mixture is stirred at −10° C. to 10° C., preferably 0° C. to 10° C. for 5 to 30 minutes, preferably 10 to 20 minutes. Alternatively, the reaction may be carried out in such that the compound (XXIX) is dissolved in $R^{90}$COHal without using any solvents, and then, the step is continued in accordance with the same manner as that described above. When the resulting product is subjected to a usual work-up, the compound (XX) can be obtained (see J. Med. Chem., 39, 3636–58 (1996)).

(Step 4)

The present step is the one for reducing the carbonyl group at 6-position of pyrrolo[1,2-a]pyrazine to transform the same into methylene. Lewis acid (for example, $AlCl_3$ and the like) is dissolved in a solvent such as methylene chloride, tetrahydrofuran and the like, a reducing agent such as boron-t-butylamine complex, sodium borohydride and the like is added to the solution at −20° C. to 10° C., preferably under ice-cooling, and the resulting mixture is stirred for 5 to 30 minutes, preferably 10 to 20 minutes. The compound (XXX) dissolved in methylene chloride, tetrahydrofuran and the like is added to the reaction mixture at −20° C. to 10° C., preferably under ice-cooling, the resulting mixture is stirred preferably for 20 to 30 minutes, and further the stir is continued at 15° C. to 40° C., preferably 20° C. to 30° C. for 1 to 5 hours, preferably 2 to 3 hours. When the resulting product is subjected to a usual work-up, the compound (XXXI) can be obtained (see J. Med. Chem., 39, 3635–58 (1996)).

(Step 5)

The present step is the one for transforming the alkyloxy group at 1-position into ketone. An acid such as concentrated hydrochloric acid and the like is added to the compound (XXXI), and the mixture is stirred at 80° C. to 150° C., preferably 100° C. to 120° C. for 1 to 5 hours, preferably 2 to 3 hours. When the resulting product is subjected to a usual work-up, the compound (XXXII) can be obtained.

(Step 6)

The present step is the one for transforming the ketone at 1-position into a halogen. A halogenating agent such as phosphorus oxychloride, phenylphosphonic dichloride and the like is added to the compound (XXII), and the mixture is refluxed for 1 to 8 hours, preferably 3 to 5 hours. When the resulting product is subjected to an ordinary work-up, the compound (XXXIII) can be obtained.

(Step 7)

The present step is the one for transforming the halogen at 1-position into ($-L^3-R^{18}$). To a suspension of $R^{18}-L^3-H$ and an alkali metal compound such as sodium and the like are added the compound (XXXIII) and sodium p-toluenesulfinate or the like, and the mixture is stirred at 70° C. to 120° C., preferably 80° C. to 100° C. for 5 to 36 hours, preferably 12 to 24 hours. When the resulting product is subjected to an ordinary work-up, the compound (XXXIV) can be obtained.

(Step 8)

The present step is the one for introducing a substituent to 8-position. The compound (XXXIV) is dissolved in a solvent such as 1,2-dichloroethane, tetrahydrofuran and the like, Hal-C(=X)—C(=Y)-Hal (for example, oxalyl chloride) and a base such as N-methylmorpholine, triethylamine and the like are added to the solution, and the mixture is stirred at 30° C. to 70° C., preferably 40° C. to 60° C. for 1 to 10 hours, preferably 3 to 6 hours. The reaction mixture is poured into cold aqueous ammonia, and the resulting mixture is stirred for 5 to 30 minutes, preferably 10 to 20 minutes. When the resulting product is subjected to an ordinary work-up, the compound (XXXVI) can be obtained.

The compounds represented by the general formula (XXIII) to (XXIV) can be synthesized by the schemes described below.

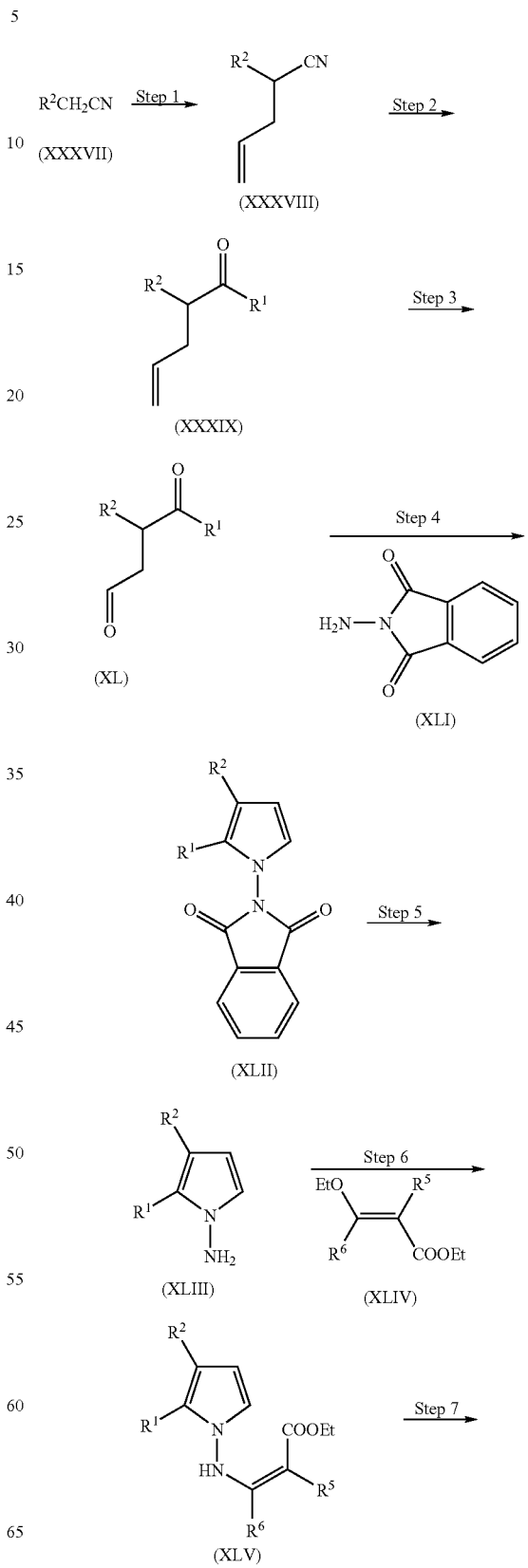

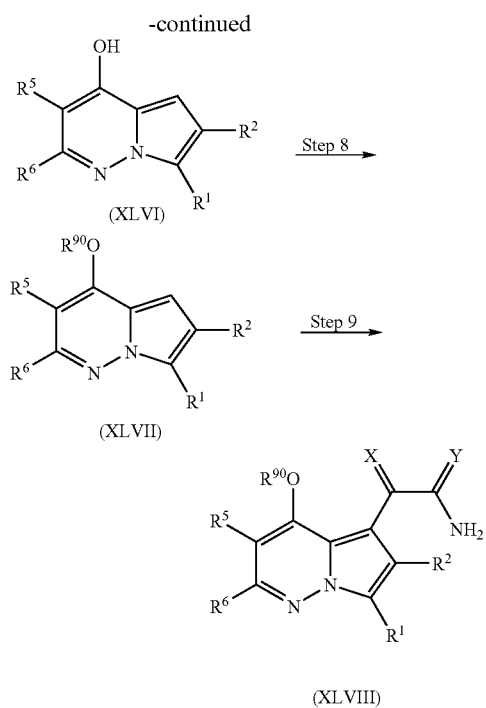

wherein $R^1$, $R^2$, $R^5$, $R^6$, X, and Y are as defined above; $R^{90}$ is an acidic group.

(Step 1)

To a solution of the compound (XXXVII) which is commercially available or is synthesized in accordance with well-known method in a solvent such as tetrahydrofuran, diethyl ether, and ethylene glycol dimethyl ether is added a base such as lithium diisopropyl amide and n-butyllithium at −78° C. to −20° C., preferably −78° C. to −60° C. To the reaction mixture is added alkenyl halide such as allyl bromide and allyl chloride at the same temperature and the resulting mixture is stirred for 1 to 24 h, preferably 1 to 8 h. After the reaction mixture is subjected to a usual work-up, the compound (XXXVIII) can be obtained (see J. Chem. Soc. Parkin. Trans. 1, 1987, 1986).

(Step 2)

To a solution of the compound (XXXVIII) in a solvent such as tetrahydrofuran, diethyl ether, and ethylene glycol dimethyl ether is added Grignard reagent ($R^1$MgHal: Hal is a halogen) at −20° C. to 0° C., preferably −15° C. to −10° C. and the resulting mixture is stirred for 1 to 15 h, preferably 1 to 8 h at −20° C. to 30° C., preferably 0° C. to 25° C. After the reaction mixture is subjected to a usual work-up, the compound (XXXIX) can be obtained (see Synthesis, 996, 1988).

(Step 3)

The present step includes ozone-oxidation of the double bond. A solution of the compound (XXXIX) in a solvent such as dichloromethane, ethyl acetate, and methanol is treated with ozone at −78° C. to 0° C., preferably −78° C. to −60° C. Without isolating the ozonide, the mixture is treated with a reducing agent such as dimethyl sulfide, triphenylphosphine, triethoxyphosphine, and zinc-acetic acid or hydrogen to give the aldehyde derivative (XL).

(Step 4)

To a solution of the compound (XL) in a solvent such as dioxane, tetrahydrofuran, and diethyl ether are added the compound (XLI) and an acid such as hydrochloric acid, sulfuric acid, and acetic acid. The resulting mixture is stirred for 0.5 to 3 h at 50° C. to 100° C. to give the pyrrole derivative (XLII) which is protected by phthalimide at N-position (Chem. Ber., 102, 3268, 1969).

(Step 5)

The present step is the one for deprotecting the phthalimide group of the compound (XLII). This step may be carried out in accordance with a usual deprotecting method as described in Protective Groups in Organic Synthesis, Theodora W Green (John Wiley & Sons). For example, to a solution of the compound (XI) in an alcohol solvent such as ethanol is added hydrazine and the resulting mixture is stirred for 0.5 to 3 h at 50° C. to 100° C. to give the amino derivative (XLIII).

(Step 6)

The present step is the one for alkylating the amino group. The compound (XLIII) and the compound (XLIV) are reacted for 10 to 60 min at 100° C. to 150° C. to give the compound (XLV) (see J. Heterocyclic Chem., 31, 409, 1994).

(Step 7)

The present step is the one for constructing pyrrolo[1,2-b]pyridazine ring. The compound (XLV) is dissolved in a solvent such as Dowtherm-A and SAS-296 and the mixture is stirred for 1 to 8 h at 150° C. to 250° C. to give the pyrrolo[1,2-b]pyridazine derivative (XLVI) (see J. Heterocyclic Chem., 31, 409, 1994). The hydroxy group at 4-position is converted into halogen by the usual method, then the halogen is may be converted into a thiol group or the like.

(Step 8)

To a solution of the compound (XLVI) in a solution such as tetrahydrofuran and dimethylformamide are added a base such as potassium carbonate and sodium hydride and $R^{26}$-Hal (Hal is halogen) and the resulting mixture is stirred for 1 to 15 h at 0° C. to 100° C., preferably 20 to 40° C. to give the compound (XLVII).

(Step 9)

The present step is the one for introducing a substituent to 5-position. The compound (XLVII) is dissolved in a solvent such as 1,2-dichloroethane, tetrahydrofuran, and Hal-C(=X)—C(=Y)-Hal (for example, oxalyl chloride) and a base such as N-methylmorpholine, triethylamine are added to the solution, and the mixture is stirred for 1 to 10 h, preferably 3 to 6 h at 30° C. to 70° C., preferably 40° C. to 60° C. The reaction mixture is poured into cold aqueous ammonia, and the resulting mixture is stirred for 5 to 30 minutes, preferably 10 to 20 minutes. After the reaction mixture is subjected to an ordinary work-up, the compound (XLVII) can be obtained.

In the examples, the following abbreviations are used.

AST: Aspartate transaminase
ALT: Alanine aminotransferase
LDH: Lactic dehydrogenase
HTBF: Hepatic tissue blood flow
min: minute
h: hour

EXAMPLE

Example 1

Measurement of Hepatic Function Related Factors by Administration before Ischemia Beagle dogs (female, 10 to 12 kg) are used for experimental animals. Under the control of general anesthesia by inserting a tube into the trachea, a bypass was formed between the portal vein, femoral vein and external jugular vein. After completely ablating the perihepatic band, the hepatoduodental ligament and inferior vena cava on and under liver are respectively clumped to prepare so called Total Hepatic Vascular Exclusion Model. An auxiliary circulation is applied during this two hour's operation. Ischemia is continued for two hours, and reperfusion of the blood is resumed by releasing the clump. Various physiological changes are confirmed under laparotomy until three hours after reperfusion and thereafter abdomen is sutured (the method for maintaining anesthesia during this period follows the existing protocol, and fluctuation of the blood pressure and the like are not corrected by different anesthetic methods). The blood is collected from the peripheral artery to measure AST, ALT and LDH as indexes of the hepatic functions. Survival at two weeks after the surgery is confirmed.

Compound (1):

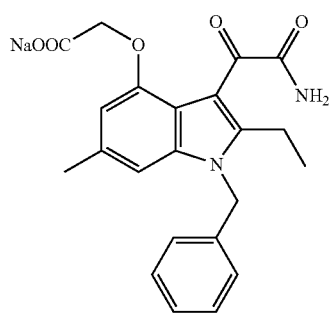

The experimental group is divided into two groups with and without administration of the compound (1). In other words, the group only the drug for maintaining anesthesia is administered is a control group, and the group the compound (1) is additionally administered is a treatment group. The control group consists of 12 animals and the treatment group 6 animals.

A dosage of 0.2 mg/kg/hr of the compound (1) was administered by continuous intravenous injection through the peripheral vein during the period of one hour from before ischemia to the occurrence of ischemia.

Figure 2:
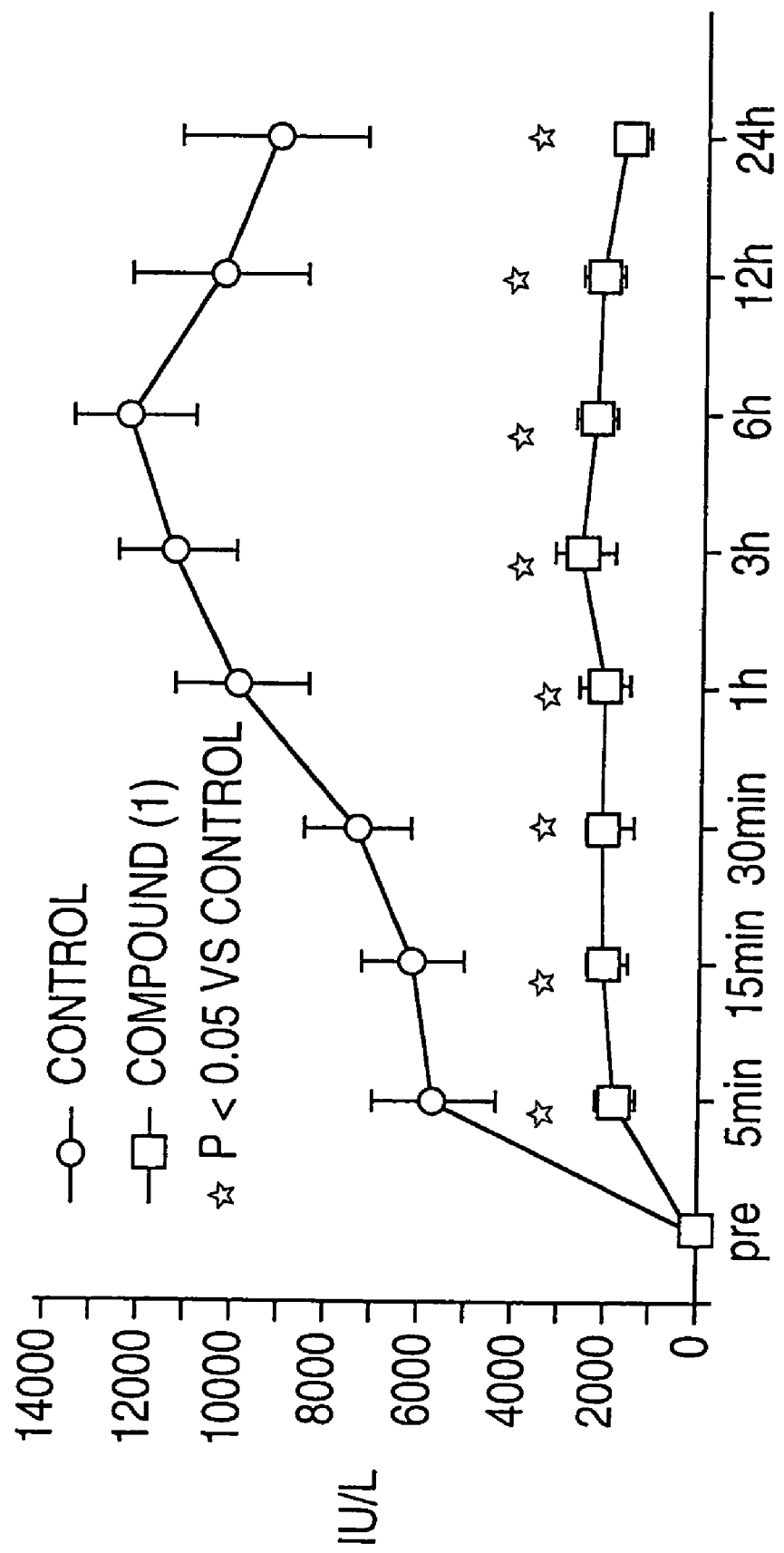
FIG. 2 is a graph showing the change of ALT as an index of hepatic functions, wherein the axis of ordinate shows the measured values (in IU/L) and the axis of abscissa shows the time after reperfusion.
Figure 3:
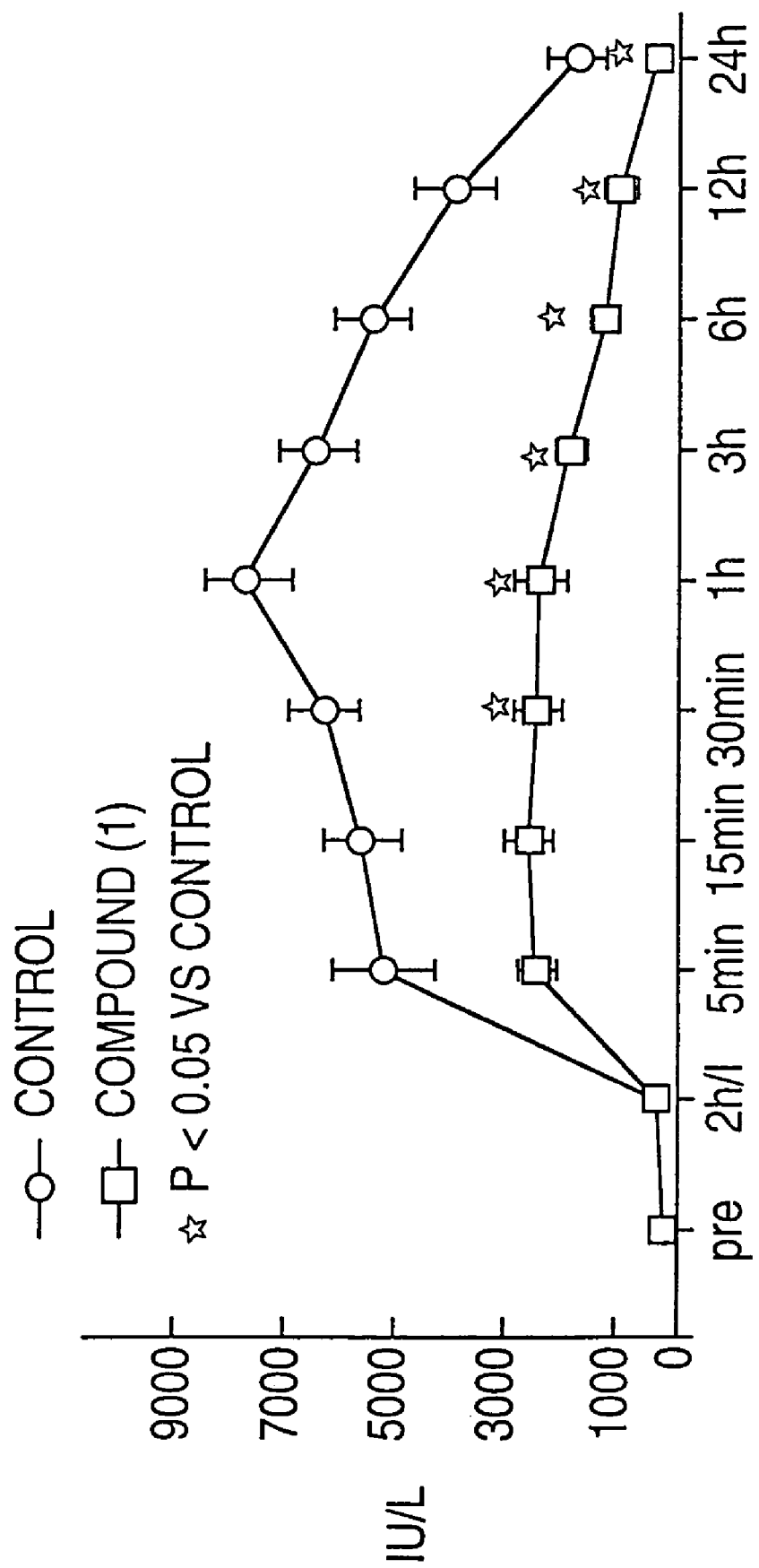
FIG. 3 is a graph showing the change of LDH as an index of hepatic functions, wherein the axis of ordinate shows the measured values (in IU/L) and the axis of abscissa shows the time (the time 2 h/I means 2 hours after ischemia and the others represent the times after perfusion).

The results are shown in FIGS. 1 to 3.

Example 2

Measurement of the Blood Flow in the Hepatic Tissue by Administration Before Ischemia The blood flow in the hepatic tissue was measured using a laser Doppler method.

Figure 4:
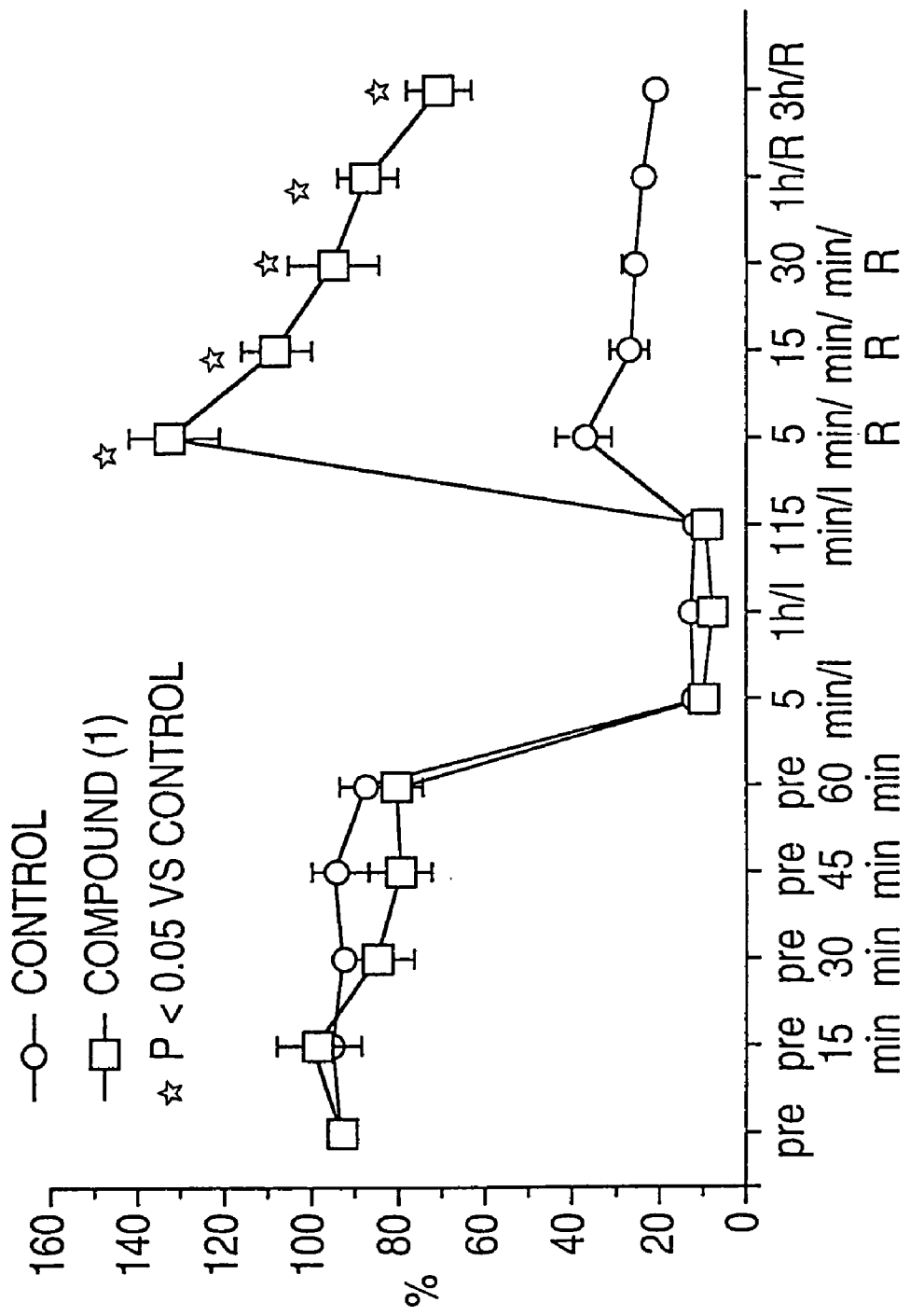
FIG. 4 is a graph showing the change of the local blood flow before and after ischemic condition, wherein the axis of ordinate shows the percentage (%) to the blood flow before ischemia and the axis of abscissa shows the time ("pre15 min" means 15 minutes after administration of the compound (1), "5 min/I" means 5 minutes after ischemia, and "5 min/R" means 5 minutes after perfusion).

The results are shown in FIG. 4.

Example 3

Measurement of the Blood Flow in the Hepatic Tissue by Administration after Ischemia The experiments were carried out by the same method as in Example 1. A dosage of 0.2 mg/kg/hr of the compound (1) was administered by continuous intravenous injection through the peripheral vein for one hour from 20 minutes before blood reperfusion to 40 minutes after the reperfusion.

Figure 5:
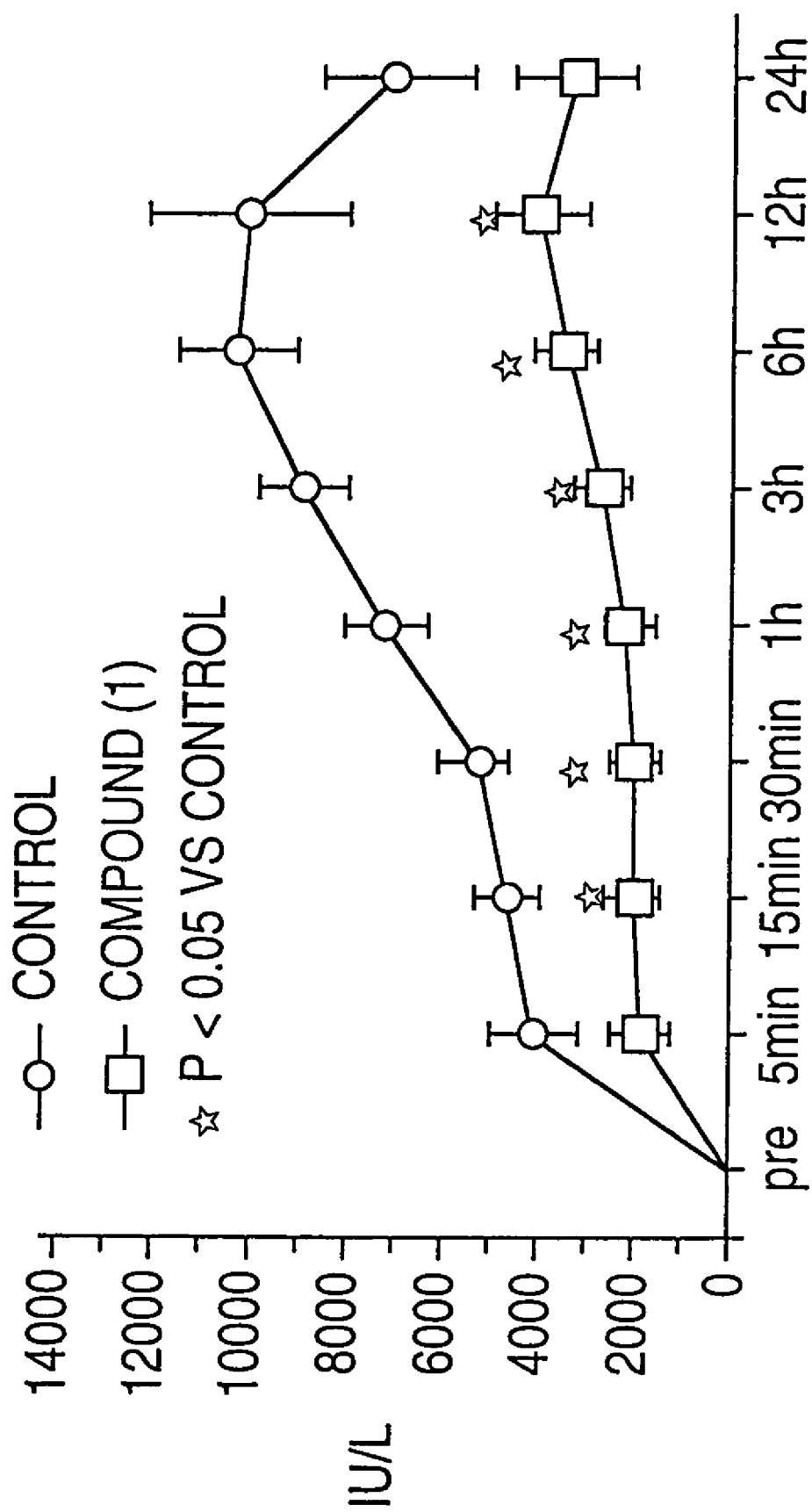
FIG. 5 is a graph showing the change of AST as an index of hepatic functions, wherein the axis of ordinate shows the measured value (in IU/L) and the axis of abscissa shows the time after reperfusion.
Figure 6:
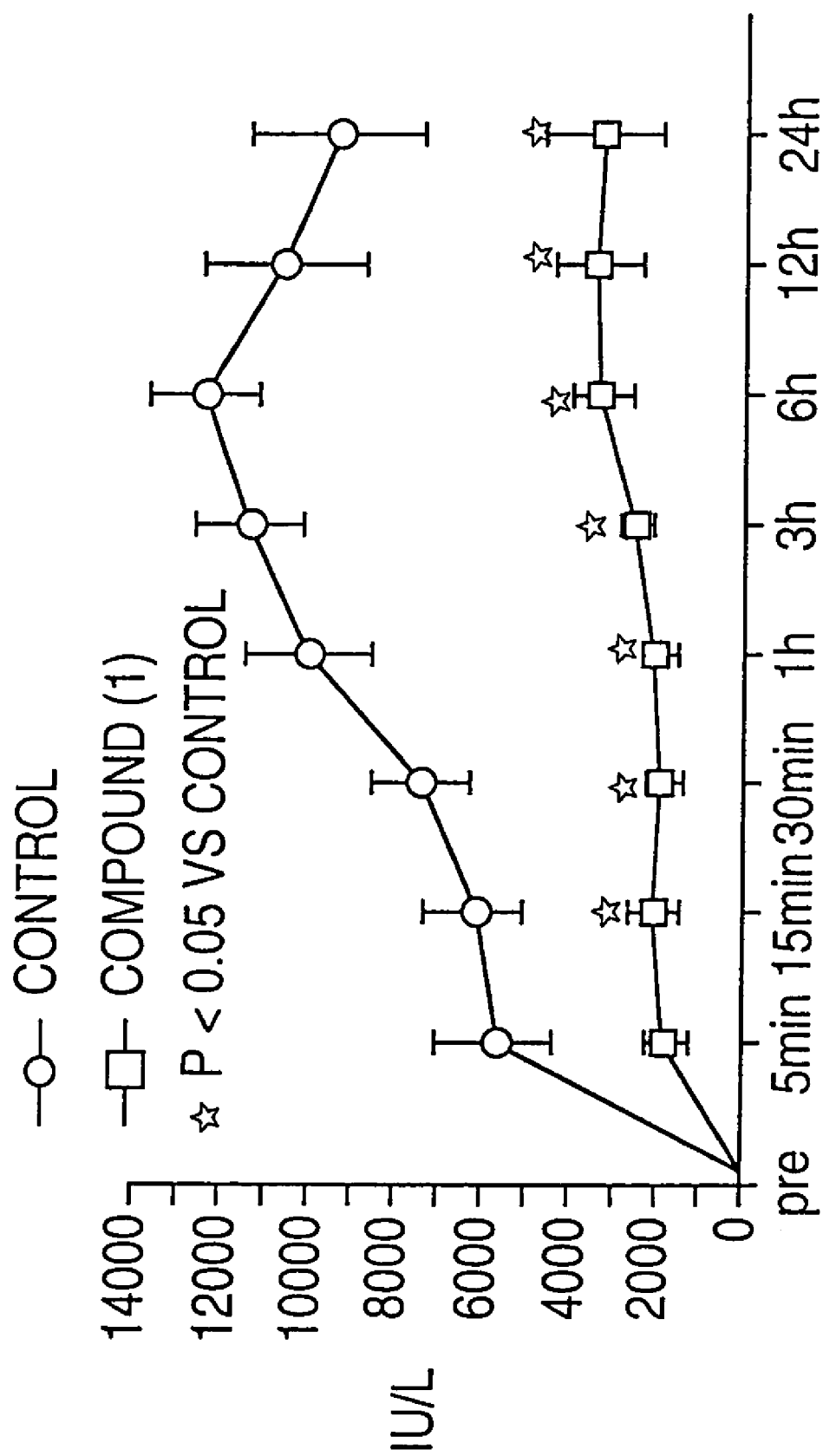
FIG. 6 is a graph showing the change of ALT as an index of hepatic functions, wherein the axis of ordinate shows the measured value (in IU/L) and the axis of abscissa shows the time (the time after reperfusion).
Figure 7:
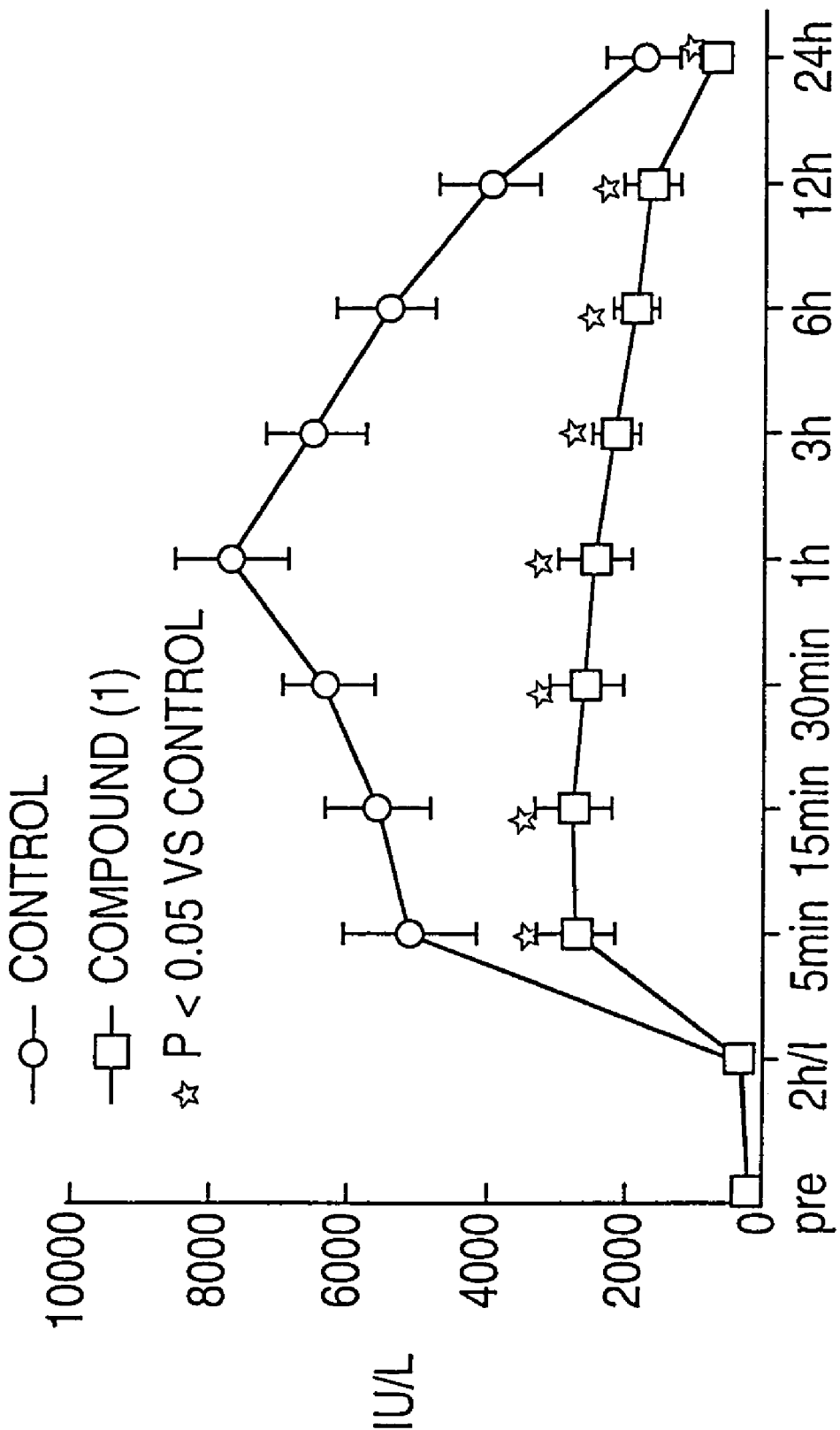
FIG. 7 is a graph showing the change of LDH as an index of hepatic functions, wherein the axis of ordinate shows the measured value (in IU/L) and the axis of abscissa shows the time ("2 h/I" means 2 hours after ischemia and the others represent the time after perfusion).

The results are shown in FIGS. 5 to 7.

Example 4

Measurement of Blood Flow in the Hepatic Tissue by Administration after Ischemia The blood flow in the hepatic tissue was measured by the same method as in Examples 2 and 3.

Figure 8:
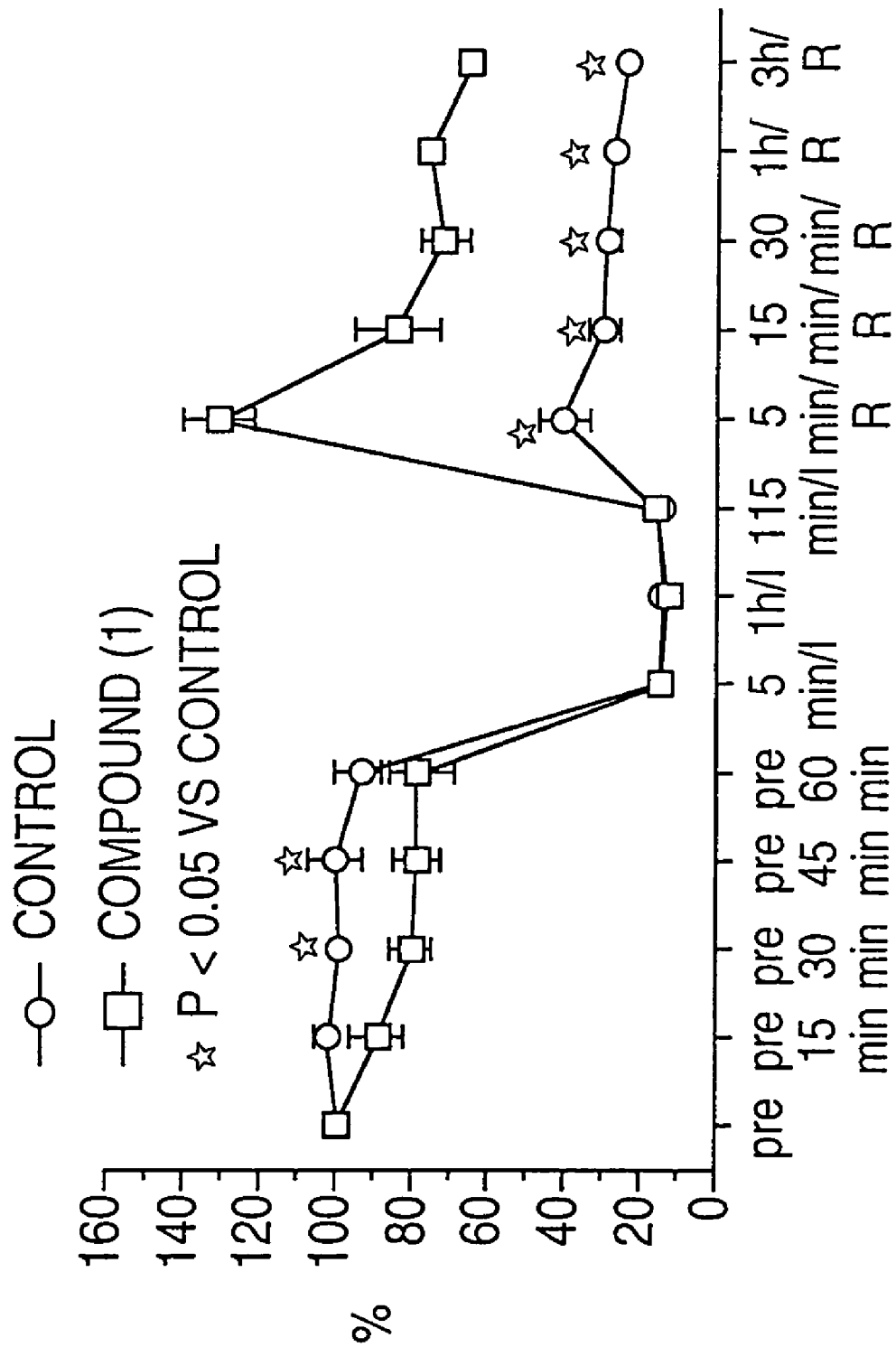
FIG. 8 is a graph showing the change of the local blood flow before and after ischemic condition, wherein the axis of ordinate shows the percentage (%) to the blood flow before ischemia and the axis of abscissa shows the time ("pre15 min" means 45 minutes before ischemia, "5 min/I" means 5 minutes after ischemia, and "5 min/R" means 5 minutes after perfusion).

The results are shown in FIG. 8.

FIG. 1 shows that the hepatic function is maintained by administration of the compound (1) before ischemia in the treatment group, since the AST value is significantly suppressed in the treatment group compared with the control group.

FIG. 2 shows that the hepatic function is maintained by administration of the compound (1) before ischemia in the treatment group, since the ALT value is significantly suppressed in the treatment group compared with the control group.

FIG. 3 shows that the hepatic function is maintained by administration of the compound (1) before ischemia in the treatment group, since the LDH value is significantly suppressed in the treatment group compared with the control group.

FIG. 4 shows that the blood flow in the liver after reperfusion is significantly increased in the treatment group administered the compound (1) before ischemia compared with the control group, in which the blood flow in the liver is decreased compared with that ischemic condition.

FIG. 5 shows that the hepatic function is maintained in the treatment group by administration of the compound (1) after ischemia, since the AST value is significantly suppressed compared with the control group.

FIG. 6 shows that the hepatic function is maintained in the treatment group by administration of the compound (1) after ischemia, since the ALT value is significantly suppressed compared with the control group.

FIG. 7 shows that the hepatic function is maintained in the treatment group by administration of the compound (1) after ischemia, since the LDH value is significantly suppressed compared with the control group.

FIG. 8 shows that the blood flow after reperfusion is significantly increased in the treatment group administered the compound (1) before ischemia as compared with the control group, in which the blood flow in the liver is decreased compared with that before ischemic condition.

Formulation Example

It is to be noted that the following Formulation Examples 1 to 8 are mere illustration, but not intended to limit the scope of the invention. The term "active ingredient" means the compound of this invention having a therapeutic or preventive action against ischemia reperfusion injuries, the prodrugs thereof, their pharmaceutical acceptable salts, or their solvates.

Formulation Example 1

Hard gelatin capsules are prepared using of the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| Active ingredient | 100 mg |
| --- | --- |
| Isotonic saline | 1000 ml |

The solution of the above ingredients generally is administered intravenously to a subject at a rate of 1 ml per minute.

INDUSTRIAL APPLICABILITY

The $PLA_2$ inhibitor according to the present invention has an action for treating or preventing ischemia reperfusion injury. Therefore, the compound is useful as the therapeutic or preventive composition in a surgery for organ transplantation and in a surgery that may cause ischemia in the organ.

The invention claimed is:

1. A method of treating ischemia reperfusion injury, which comprises administering to a subject in need thereof a sPLA2 inhibitor, wherein the ischemia reperfusion injury occurs in liver, and wherein the sPLA2 inhibitor is selected from the group consisting of

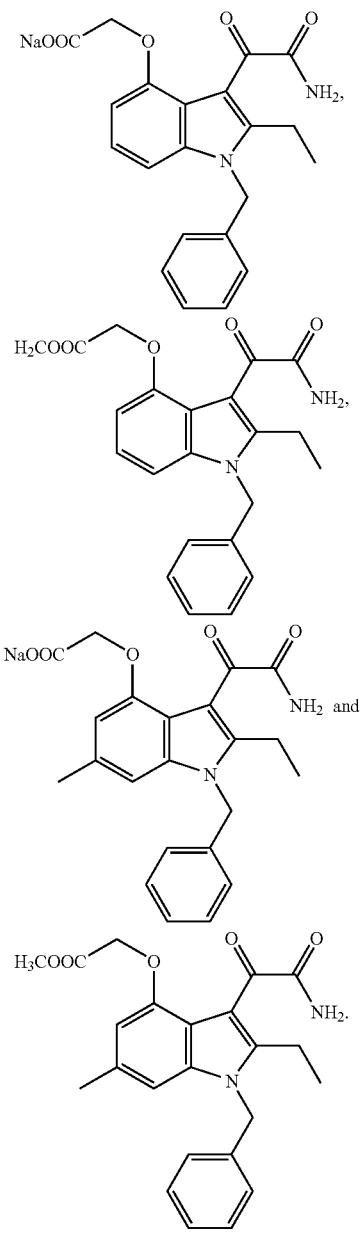

* * * * *